(12) United States Patent
Karlsson-Parra et al.

(10) Patent No.: US 10,626,371 B2
(45) Date of Patent: Apr. 21, 2020

(54) CO-DIFFERENTIATION OF MONOCYTES FROM ALLOGENEIC DONORS

(71) Applicant: Immunicum AB, Göteborg (SE)

(72) Inventors: Alex Karlsson-Parra, Uppsala (SE); Bengt Andersson, Mölndal (SE)

(73) Assignee: IMMUNICUM AB, Gothenburg (SE)

( * ) Notice: Subject to any disclaimer, the term of this patent is extended or adjusted under 35 U.S.C. 154(b) by 25 days.

(21) Appl. No.: 15/623,530

(22) Filed: Jun. 15, 2017

(65) Prior Publication Data

US 2017/0321189 A1    Nov. 9, 2017

Related U.S. Application Data

(62) Division of application No. 14/653,184, filed as application No. PCT/EP2013/077139 on Dec. 18, 2013, now Pat. No. 9,714,413.

(30) Foreign Application Priority Data

Dec. 18, 2012    (EP) .................................... 12197687

(51) Int. Cl.
*A61K 35/15* (2015.01)
*C12N 5/0784* (2010.01)
(52) U.S. Cl.
CPC ............ *C12N 5/0639* (2013.01); *A61K 35/15* (2013.01); *C12N 2500/40* (2013.01); *C12N 2501/22* (2013.01); *C12N 2501/2304* (2013.01); *C12N 2501/24* (2013.01); *C12N 2506/115* (2013.01)
(58) Field of Classification Search
CPC .................................................... A61K 35/15
See application file for complete search history.

(56) References Cited

FOREIGN PATENT DOCUMENTS

| EP | 1509244 | 3/2005 |
|---|---|---|
| WO | WO-2001/051617 A1 | 7/2001 |
| WO | WO-2003/010292 A2 | 2/2003 |
| WO | WO-2011/098516 A1 | 8/2011 |

OTHER PUBLICATIONS

Sallusto et al. (J. Exp. Med. Apr. 1, 1994; 179 (4): 1109-18).*
Hackstein et al. (Cell. Immunol. 2011; 271 (2): 401-12).*
Shi et al. (Mediators Inflamm. 2015; 2015: 984690; pp. 1-8).*
Von Bubnoff et al. (J. Immunol. Jun. 15, 2011; 186 (12): 6701-9).*
Anguille et al. (J. Transl. Med. Dec. 18, 2009; 7: 109; pp. 1-16).*
Alder, J., et al. (2008), "Allogeneic Monocyte-Derived Cells Loaded with Tumor Antigens as a Combined Antigen-Delivery Vehicle and Adjuvant in Cancer Immunotherapy", *Cancer Immunol Immunother*, 57(Suppl 1): S1-S53, P028.
Ebner, S., et al. (2001), "Generation of Large Numbers of Human Dendritic Cells from Whole Blood Passage through Leukocyte Removal Filters: an Alternative to Standard Buffy Coats", *Journal of Immunological Methods*, 252: 93-104.
Edlich, B., et al. (2010), "Dendritic Cells Transfected with Her2 Antigen-Encoding RNA Replicons Cross-Prime CD8 T Cells and Protect Mice Against Tumor Challenge", *Vaccine*, 28: 7764-7773.
European Search Report dated Aug. 12, 2013 issued in European patent application No. 12197687.2.
International Search Report and Written Opinion dated Apr. 3, 2014 issued in PCT application No. PCT/EP2013/077139.
Lakkis, F., et al. (2013), "Origin and Biology of the Allogeneic Response", *Cold Spring Harbor Perspectives in Medicine*, 3(8): 1-11.
Langenkamp, A., et al. (2000), "Kinetics of Dendritic Cell Activation: Impact on Priming of TH1, TH2 and Nonpolarized T Cells", *Nature Immunology*, 1(4): 311-316.
Laurin D., et al. (2004), "Allogeneic Reaction Induces Dendritic Cell Maturation Through Proinflammatory Cytokine Secretion", *Transplantation*, 77(2): 267-275.
Megiovanni, A., et al. (2006), "Polymorphonuclear Neutrophils Deliver Activation Signals and Antigenic Molecules to Dendritic Cells: a New Link between Leukocytes Upstream of T Lymphocytes", *Journal of Leukocyte Biology*, 79: 977-988.
Meyer, T., et al. (2005), "Filter Buffy Coats (FBC): A Source of Peripheral Blood Leukocytes Recovered from Leukocyte Depletion Filters", *Journal of Immunological Methods*, 307: 150-166.
Napolitani, G., et al. (2005), "Selected Toll-Like Receptor Agonist Combinations Synergistically Trigger a T Helper Type 1-Polarizing Program in Dendritic Cells", *Nature Immunology*, 6(8): 769.
Park, S., et al. (2012), "TNF Induces Endotoxin Tolerance Mediated by GSK3 in Macrophages", *Nat. Immunol*, 12(7): 607-615.
Reiser, C., et al. (1998), "Differential Deactivation of Human Dendritic Cells by Endotoxin Desensitization: Role of Tumor Necrosis Factor-α and Prostaglandin E2", *Blood*, 91(9):3112-3117.
Sallusto et al. (1994) "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor" J. Exp. Med., 179(4): 1109-18.
Sallusto, F., et al. (1999), "Distinct Patterns and Kinetics of Chemokine Production Regulate Dendritic Cell Function", *Eur. J. Immunol.*, 29:1617-1625.
Schwanke, U., et al. (2006), "Isolation of Monocytes from Whole Blood-Derived Buffy Coats by Continuous Counter-Flow Elutriation", *Journal of Clinical Apheresis*, 21:153-157.
Siders, W., et al. (2009), "Induction of Antitumor Immunity by Semi-Allogeneic and Fully Allogeneic Electrofusion Products of Tumor Cells and Dendritic Cells", *CTS*, 2(1): 75-79.

(Continued)

*Primary Examiner* — Stephen L Rawlings
(74) *Attorney, Agent, or Firm* — Harness Dickey & Pierce P.L.C.

(57) ABSTRACT

Disclosed is a method of producing non-exhausted immature dendritic cells (DCs) originating front at two different, allogeneic donors. In the method, a mixture of allogeneic leukocytes, which allogeneic leukocytes have been obtained from at least two different, allogeneic donors is provided. Subsequently, allogeneic monocytes are isolated from the mixture of allogeneic leukocytes. Thereafter, non-exhausted immature DCs are generated from said isolated allogeneic monocytes.

11 Claims, 21 Drawing Sheets

(56) References Cited

OTHER PUBLICATIONS

Wallgren, A., et al. (2005), "Direct Allorecognition Promotes Activation of Bystander Dendritic Cells and Licenses Them for Th1 Priming: A Functional Link Between Direct and Indirect Allosensitization", *Scandinavian Journal of Immunology*, 62: 234-242.

Zahorchak, A., et al. (2007), "Infusion of Stably Immature Monocyte-Derived Dendritic Cells Plus CTLA4lg Modulates Alloimmune Reactivity in Rhesus Macaques", *Transplantation*, 84(2): 196-206.

Zecher, D., et al. (2009), "An Innate Response to Allogeneic Noneself Mediated by Monocytes", *The Journal of Immunology*, 183: 7810-7816.

Zeng, Q., et al. (2012), "Innate Recognition of Allogeneic Non-Self Induces Monocyte Differentiation to Mature Dendritic Cells in Vivo", *Am J Transplant*, 12: 148.

Jonuleit H. et al., (1997) "Pro-inflammatory cytokines and prostaglandins induce maturation of potent immunostimulatory dendritic cells under fetal calf serum-free conditions" Eur. J. Immunol 27:3135-3142.

P. V. Phuc et al., "Production of functional dendritic cells from menstrual blood—a new dendritic cell source for immune therapy," In Vitro Cell. Dev. Biol.—Animal, 47:368-375 (2011).

* cited by examiner

CO-DIFFERENTIATION OF MONOCYTES FROM ALLOGENEIC DONORS

PRIORITY STATEMENT

This application is a divisional patent application of U.S. application Ser. No. 14/653,184 filed on 17 Jun. 2015, which is a U.S. National Stage Application under 35 U.S.C. § 371 of PCT International Application No. PCT/EP2013/077139, which has an International filing date of 18 Dec. 2013 and which claims priority to European Application No. 12197687.2 filed 18 Dec. 2012. The contents of each application recited above are incorporated herein by reference in their entirety.

FIELD OF THE INVENTION

The present invention relates to a method for producing non-exhausted immature monocyte-derived human dendritic cells (DC).

BACKGROUND

Traditional cancer therapies, such as surgery, radiation, and chemotherapy, are often insufficient in treating patients and usually cause severe side effects.

Immunotherapy has shown promise as an alternative treatment method with less negative side effects.

It is now well established that the immune system has cells, particularly CD8+ cytotoxic T lymphocytes (CTLs), which can recognize and potentially kill tumor cells. Nevertheless, a major problem is that the killing ability of these T cells are either not induced or only weakly induced in cancer patients. One possibility is that there is inadequate tumor antigen presentation and co-stimulation by dendritic cells (DCs), "nature's adjuvant" for eliciting a functional and tumor-specific T cell immunity in cancer patients.

Existing cancer immunotherapy strategies mainly focus on antigen-loaded autologous, patient-derived DCs, which have been differentiated and antigen-loaded ex vivo. The underlying premise of this approach is that the efficiency and control provided by ex vivo manipulation of the DCs generates DCs with strong antigen-presenting and co-stimulatory capacity. The quality of the T cell response depends on the ability of these autologous DCs to present tumor antigens to T cells in a MHC-restricted manner (DCs and T cells have to be from the same individual) in draining lymph nodes and thus create a tumor-specific T cell response.

Monocyte-derived, autologous DCs are the most commonly used DCs in pilot studies, as it is possible to obtain billions of monocytes from peripheral blood leukocytes collected by leukapheresis, a laborious and time-consuming procedure in which white blood cells are separated from circulating blood. Several methods are available to subsequently enrich monocytes and two of these methods, elutriation and antibody/bead isolation, can also be performed in conformity with Good Manufacturing Practice (GMP) guidelines.

The monocytes are subsequently cultivated in media supplemented with GM-CSF and IL-4 for 4-7 days, leading to their differentiation into immature DCs, which immature DCs are characterized by their outstanding capacity to produce large amounts of pro-inflammatory chemokines and cytokines upon subsequent stimulation with certain types of activating factors (Sallusto et al, Eur J Immunol, 1999. 29:1617; Napolitani et al, Nature Immunology 2005. 6:769). The stimulated DCs are usually pre-pulsed with relevant tumor antigen(s) and activated for 1-2 days before vaccination. However, the immune responses to such DC-based vaccines are often weak, and clinical responses are rarely complete and long lasting.

Little has been known regarding the fate and function of ex vivo generated autologous DCs after they have been injected. In the human setting, the migration pattern of injected vaccine DCs was recently tracked in vivo and notably, less than 5% of the injected DCs reached the draining lymph nodes while the majority of DCs remained at the injection site. These locally trapped vaccine DCs rapidly lost their viability and were subsequently cleared by recruited antigen-presenting cells.

Data has now been provided that injected vaccine DCs that have been activated ex vivo during a limited time-period (i.e. 6 to 18 h) become pro-inflammatory (PI) DCs, which are able to indirectly prime native CD8+ T cells in vivo by acting as a pure local immune adjuvant. This adjuvant function of injected PI-DCs is strictly dependent on their ongoing secretion of certain DC and NK-cell recruiting chemokines at the time of administration (after removal of activating factors). Such PI-DCs also express/secrete factors that induce activation of recruited endogenous NK-cells and DCs at the vaccination site. In contrast to PI-DCs, long-time (i.e. >24 h) activated DCs, which have been commonly used in clinical trial, are characterized by their "exhausted" state (Langenkamp et al 2000), and therefore unable to secrete desirable chemokines and DC-activating factors at the time of administration.

In conclusion, PI-DCs not only can act as direct stimulators of MHC-compatible autologous T cells but also act as an adjuvant producing large quantities of pro-inflammatory chemokines and cytokines at the time of administration. Local injection of PI-DCs will lead to recruitment and activation of other immune cells, including circulating NK cells and DC-precursors. If the injected PI-DCs have been preloaded with relevant tumor antigens or injected directly into an existing tumor lesion, recruited endogenous DCs will engulf dying vaccine cells expressing relevant tumor antigens or dying antigen-expressing tumor cells, respectively. After activation these recruited and subsequently antigen-loaded endogenous DCs will migrate to draining lymph nodes were they prime tumor-specific T cells in a MHC-restricted manner (Liu et al, 2008). This conclusion is supported by data from several recent pre-clinical studies in which tumor growth was significantly reduced by therapeutic vaccinations with non-exhausted MHC-incompatible, allogeneic PI-DCs (Alder et al 2008, Siders et al 2009, Edlich et al 2010)

The strong adjuvant function by PI-DCs, which importantly don't require MHC-compatibility between PI-DCs and patient T cells, therefore introduces the possibility of using pre-produced and freeze-stored MHC-incompatible, allogeneic, PI-DCs as "off the shelf" vaccines, representing a viable, practical alternative to the current custom-made, patient-specific DC vaccines. The use of such MHC-incompatible, allogeneic, PI-DCs is disclosed in EP 1 509 244 B1 and WO 2011/098516.

For ethical reasons, large scale procurement of monocytes from normal blood donors by leukapheresis for the sole purpose of commercial large-scale vaccine production for clinical use is not feasible. In practice, the available raw material, i.e. monocytes, for PI-DC production is therefore restricted to monocytes obtained from waste-product (buffy coats and/or used leukocyte depeltion filteers) in the course of separating unwanted leukocytes from different whole blood components or monocytes obtained from buffy coats at blood banks.

However, the total number of monocytes which can be isolated from each buffy coat or from each blood bag-leukocyte depletion filter is usually less than 200 millions (Ebner S et al., *Generation of large numbers of human dendritic cells from whole blood passaged through leukocyte removal filters: an alternative to standard buffy coats* J Immunol Methods 252 (2001), leading to unacceptable high costs for enrichment and subsequent DC-differentiation of separate batches of monocytes (each batch derived from one single donor) with methods that are in conformity with Good Manufacturing Practice (GMP) guidelines according to the art.

Thus, there is a need in the art for a method for large scale and cost-effective clinical grade production of non-exhausted immature dendritic cells from monocyte-containing waste-product derived from blood banks.

SUMMARY

Consequently, the present invention seeks to mitigate, alleviate, eliminate or circumvent one or more of the above-identified potential deficiencies in the art and disadvantages singly or in any combination by providing a method a method of producing non-exhausted immature dendritic cells (DCs) originating from at least two different, allogeneic donors. In the method, a mixture of allogeneic leukocytes, which allogeneic leukocytes have been obtained from at least two different, allogeneic donors is provided. Subsequently, allogeneic monocytes are isolated from the mixture of allogeneic leukocytes to provide monocyte-enriched allogeneic leukocytes. Thereafter, non-exhausted immature DCs are generated from the monocyte-enriched allogeneic leukocytes, by co-culturing the monocyte-enriched allogeneic leukocytes for 2 to 7 days in aqueous cell culture medium free from non-human serum. The medium is supplemented with interleukin-4 (IL-4) and granulocyte-macrophage colony stimulating factor (GM-CSF).

In contrast to the prevailing prejudice, the generated monocyte-derived immature dendritic cells are non-exhausted and thus able to produce substantial amounts of pro-inflammatory chemokines and pro-inflammatory cytokines in a sustained fashion subsequent to activation into pro-inflammatory DCs. Thus, the method represents a large scale and cost-effective clinical grade production method of non-exhausted immature dendritic cells.

A further aspect of the invention relates to a mixture of allogeneic non-exhausted immature dendritic cells (DCs) originating from at least two different, allogeneic donors. Such a mixture is obtainable by the described method.

A further aspect of the invention relates a method of producing pro-inflammatory DCs. By activating the non-exhausted immature DCs pro-inflammatory DCs are obtained. By such a method, a mixture of allogeneic pro-inflammatory dendritic cells originating from at least two different, allogeneic donors is obtainable. The mixture may be formulated into pharmaceutical composition further comprising at least one pharmaceutical acceptable carrier. The mixture and the pharmaceutical composition, respectively, may be used the treatment of cancer.

Further advantageous features of the invention are defined in the dependent claims. In addition, advantageous features of the invention are elaborated in embodiments disclosed herein.

DETAILED DESCRIPTION OF PREFERRED EMBODIMENTS

The present inventors did envisage that monocyte-containing leukocyte populations which are present in buffy coats or trapped in leukocyte removal filters used for depleting leukocytes from whole blood (used for enrichment of red blood cells) or leukocyte removal filters used for depleting leukocytes from pooled buffy coats (used for enrichments of platelets), could potentially be used for large-scale and cost-effective production of non-exhausted immature dendritic cells.

As previously shown, leukocytes retained by different types of leukocyte removal filters can be recovered by back-flushing with a suitable medium followed by monocyte enrichment (Ebner S et al., *Generation of large numbers of human dendritic cells from whole blood passaged through leukocyte removal filters: an alternative to standard buffy coats* J Immunol Methods 252 (2001) 93-104; and Meyer T P H et al., Filter Buffy Coats (FBC): *A source of peripheral blood leukocytes recovered from leukocyte depletion filters*. J Immunol Methods 307 (2005) 150-166).

A buffy coat is the fraction of an anti-coagulated blood sample that contains most of the leukocytes, including neutrophils, basophils, eosinophils, monocytes, and lymphocytes, and platelets following density gradient centrifugation of whole blood. Buffy coats are normally used as raw material for platelet production. During this process, leukocyte reduction by a leukocyte depletion filter is performed after pooling of 4 to 8 buffy coats. Typically, the TACSI equipment or the OrbiSac system is used for platelet isolation from buffy coats.

The TACSI equipment for platelet preparation from pooled buffy coats contains a system box (fixed on the rotor) and an insert that can be removed for the mounting of the TACSI kit. Each system box is provided with a press system, controlled and monitored by an individual microprocessor. In a first sequence, pooled buffy coats within the pooling container are sedimented by centrifugation in a vertical position. In the following step, the platelet-rich layer (also containing a substantial amount of leukocytes, including monocytes and lymphocytes) of the pooled buffy coat supernatant is transferred into a storage container by the activation of the press system in each box. In addition, the filter for leukodepletion is integrated in the TACSI kit between the processing bag and the final storage container. The leukocyte depletion filter and the rest of the buffy coat within the buffy coat pooling container, both containing substantial amount of monocytes, are then discharged.

In the alternative OrbiSac system for automated platelet enrichment, the buffy coat pooling container is ring-shaped. After centrifugation, the platelet-rich central part of the supernatant is transferred into a container placed in the center of the centrifuge and the transfer is made through an integrated leukocyte depletion filter. The leukocyte depletion filter and the rest of the buffy coat within the buffy coat pooling container, both containing substantial amount of monocytes, is then discharged.

In summary, methods in the art for platelet enrichment from buffy coats provide two possible sources of monocytes, i.e. the rest of the buffy coat being depleted of platelets, also denoted platelet depleted buffy coat, and the leukocyte depletion filter. The platelet depleted buffy coat and the leukocyte depletion filter each contains a mixture of leukocytes, including up to 1 billion monocytes. However, these monocytes are allogeneic with respect to each other, as they origin from different, allogeneic donors, due to the pooling of buffy coat prior to the platelet depletion.

Un-pooled buffy coats, containing platelets, or filters obtained after leukocyte depletion of whole blood will maximally only provide up to about 100 to 200 millions monocytes per buffy coat or filter. Therefore they must be pooled in order to provide a number sufficient for cost-effective GMP-production of non-exhausted immature DCs.

Similar to leukocytes obtained from platelet production pooled leukocytes from buffy coats, containing platelets, or from filters used to deplete whole blood from leukocyte will also consist of a mixed cell population originating from different allogeneic donors.

Pooling of leukocytes from at least 5 to 10 buffy coats or pooling of eluted leukocytes from at least 5 to 10 whole blood leukocyte filters would, at least theoretically, solve the problem of providing a sufficient number of leukocytes for large-scale and cost-effective clinical grade production of non-exhausted immature DCs.

Similarly, pooled, platelet depleted buffy coats and/or leukocyte depletion filters used for platelet enrichment from buffy coats, can potentially be used to provide a sufficient number of leukocytes for large-scale and cost-effective clinical grade production of non-exhausted immature DCs.

As previously shown, leukocytes retained by leukocyte depletion filters can be recovered by back-flushing with a suitable medium followed by monocyte enrichment (Ebner S et al., *Generation of large numbers of human dendritic cells from whole blood passaged through leukocyte removal filters: an alternative to standard buffy coats* J Immunol Methods 252 (2001) 93-104; and Meyer T P H et al., Filter Buffy Coats (FBC): *A source of peripheral blood leukocytes recovered from leukocyte depletion filters*. J Immunol Methods 307 (2005) 150-166).

However, an envisaged problem associated with the subsequent co-culturing of monocyte-enriched leukocytes, which are derived from different, allogeneic donors, is that their incompatibility as to major histocompatibility complex (MHC) class I and class II antigens is deemed to lead to a premature activation of monocytes/immature DCs from one donor by contaminating alloreactive T cells and/or natural killer cells from another donor.

Co-culturing in standard cell culture medium, such as RPMI-1640 (RPMI=Roswell Park Memorial Institute, at which institute the medium original was developed by Moore et. al.) with fetal calf serum, or in serum-free cell culture medium, such as X-VIVO 15, of mononuclear cells, including monocytes, lymphocytes and NK-cells, from two allogeneic donors is known to induce production of well-known DC-activating factors, including TNF-alpha (Laurin et al, Transplantation 2004; 77:267; Wallgren et al, Scand J Immunol 2005; 62:234). Further, addition of culture supernatants from such co-cultures in standard RPMI-1640 medium with fetal calf serum or standard serum-free medium of allogeneic mononuclear cells have repeatedly been shown to induce activation/maturation of monocyte-derived, immature, DCs (Laurin et al, Transplantation 2004; 77:267; Wallgren et al, Scand J Immunol 2005; 62:234).

Furthermore, addition of TNF-alpha to standard RPMI-1640 media supplemented with GM-CSF and IL-4 used for differentiation of monocytes into immature DCs has been shown to induce premature activation and subsequent exhaustion (tolerance) of differentiated DCs (Rieser C et al., Differential Deactivation of Human Dendritic Cells by Endotoxin Desensitization: Role of Tumor Necrosis Factor-α and Prostaglandin E2. Blood 91 (1998) 3112-3117).

The problem with contaminating T cells and NK cells is of relevance even after GMP-enrichment (elutriation and antibody/bead isolation) of monocytes from pooled buffy coats or from leukocyte deletion filters (Schwanke et al, Journal of Clinical Apheresis 21: 153-157 (2006); Meyer et al, Journal of Immunological Methods 307 (2005) 150-166) due to the difficulty in preparing monocyte cell populations essentially free from contaminating T cells and NK cells.

Furthermore and importantly, not only co-culturing with allogeneic lymphocytes in standard medium, but also co-culturing of monocytes with allogeneic neutrophils in RPMI-1640 media supplemented with fetal calf serum, results in up-regulation of membrane CD40, CD86, and human leukocyte antigen (HLA)-DR on DCs, i.e. premature activation, as has been shown by Meggiovanni et al (cf. Journal of Leukocyte Biology, 2006; 79; 977-988). Substantial removal of neutrophils from monocytes within pooled buffy coats or eluted filter leukocyes using elutriation (Schwanke et al, Journal of Clinical Apheresis 21: 153-157 (2006)) or anti-body/bead isolation (Meyer et al, Journal of Immunological Methods 307 (2005) 150-166) has been shown to be very difficult. Usually such a monocyte-enriched product contains a significant amount (i.e. 25-40% based on the total number of cells present) of neutrophils. From a safety perspective this neutrophil contamination is however not a problem.

Moreover, even if it was possible to prepare 100% pure monocyte cell populations, this would not eliminate the risk of premature activation due to active interactions between monocytes from different, allogeneic donors. In a recent review paper entitled "*Origin and biology of the allogeneic response*", by the distinguished and renowned immunologists Fadi G. Lakkis and Robert I. Lechler (cf. Cold Spring Harbor perspectives in medicine, Vol. 3, No. 8, 2013) it was conclude that an innate allorecognition mechanisms indeed exist. The authors state that: "*Allograft rejection is not restricted to vertebrate animals endowed with adaptive immune systems, but is common to many invertebrate organisms that predate the evolution of adaptive immunity (animals that lack T and B lymphocytes, NK cells, somatic gene rearrangement enzymes, and the MHC)*".

Furthermore, and perhaps more direct, allogenic responses are seen also in mice devoid of lymphoid cells. Activation of monocytes is dependent on differences in non-MHC antigens between recipient monocytes and injected allogeneic donor leukocytes, including allogeneic monocytes (Zecher D et al., An Innate Response to Allogeneic Nonself Mediated by Monocytes. J Immunol 83 (2009) 7810-7816). Zecher et al. showed that injecting allogeneic leukocytes into the ear pinnae of RAG2/2 mice, lacking T and B lymphocytes, elicits significantly greater swelling and infiltration of the skin with host myeloid cells than injecting syngeneic leukocytes. The response to the allogeneic leukocytes occurred independently of NK cells and was mediated by monocytes. Further, the monocyte response was to allodeterminants not linked to the MHC.

In an even more recent paper (Zeng Q, et al. "*Innate recognition of allogeneic non-self induces monocyte differentiation to mature dendritic cells in vivo.*" Am J Transplant 12: 148-148, 2012), the authors showed that heart allografts transplanted to gc2/2RAG2/2 mice, which lack T, B, and NK cells, are rapidly infiltrated by host monocytes that differentiate into mature, IL-12-expressing dendritic cells (DCs). The determinants on allogeneic cells that trigger host monocyte maturation, and the putative monocyte receptors that recognize them, are however not known yet.

There is thus clear evidence that mammalian monocytes directly respond to non-MHC determinants on allogeneic cells independently of T, B, and NK cells. Hence, according to the generally prevailing perception, alloreactivity is deemed to be a general property of monocytes.

Taken together, this implies that co-culturing of monocyte-enriched cell populations derived from different allogeneic donors clearly is envisaged to lead to pre-activation and subsequent exhaustion of the monocytes during their differentiation into monocyte-derived DCs. Thereby the DCs will be unable to become PI-DCs producing required adjuvant factors in a sustained fashion when re-stimulated with relevant activating factors.

This envisaged activation-induced exhaustion is similar to the well-known exhaustion of monocytes, macrophages and DCs that is induced by a premature activation with inflammatory agents like TNF-α (Park et al, Nat Immunol. 2012; 12: 607-615) or microbial lipopolysaccharides (LPS) (Rieser C et al., Differential Deactivation of Human Dendritic Cells by Endotoxin Desensitization: Role of Tumor Necrosis Factor-α and Prostaglandin E2. Blood 91 (1998) 3112-3117; Langenkamp A et al., Kinetics of dendritic cell activation: impact on priming TH1, TH2 and nonpolarized T cells. Nature Immunol. 1 (2000) 311-316).

The present inventors have however surprisingly found that non-exhausted immature DCs actually can be propagated from an initial cell population consisting of a mixture of allogeneic monocyte-enriched leukocytes from different, allogeneic donors, in a manner similar to the one used to propagate non-exhausted immature DCs from enriched monocytes which are derived from one single donor (cf. WO 2011/098516), i.e. by use of an aqueous cell culture medium free from non-human serum, but supplemented with interleukin-4 (IL-4) and granulocyte-macrophage colony stimulating factor (GM-CSF).

In contrast to the prevailing prejudice, propagation of a mixture of enriched monocytes from different, allogeneic donors into immature DCs under certain conditions was surprisingly shown to not result in premature activation and subsequent exhaustion of the DCs. These conditions include co-culturing in aqueous cell culture medium free from non-human serum and supplemented with GM-CSF and IL-4.

However, co-culturing in aqueous cell culture medium free from non-human serum and not supplemented with interleukin-4 (IL-4) and granulocyte-macrophage colony stimulating, as well as co-culturing in aqueous cell culture medium comprising non-human serum, e.g. bovine calf serum, and supplemented with interleukin-4 (IL-4) and granulocyte-macrophage colony do, as expected and recognized in the art, result in premature activation and subsequent exhaustion of the DCs.

Thus, monocytes may be isolated from pooled leukocyte populations from different allogeneic donors, making it possible to perform large-scale and cost-effective GMP-enrichment of monocytes, such as elutriation (Elutra) or antibody/bead-isolation (CliniMacs). Subsequently, non-exhausted immature DCs can be generated from the isolated monocyte-enriched allogeneic leukocytes without premature activation.

Such non-exhausted immature DCs may be used to propagate pro-inflammatory-DCs which are aimed to function as an anti-tumor vaccine when injected intratumorally (cf. WO 2011/098516). Further, non-exhausted immature DCs from different, allogeneic donors, may be loaded with tumor antigen(s) before activation in order to produce a "complete" cellular allogeneic anti-cancer vaccine (cf. EP 1 509 244 B1) that can be injected into different sites, including intratumoral, subcutaneous, epicutaneous, intramuscular and/or intravenous sites.

An embodiment thus relates to a method for producing non-exhausted immature DCs from a mixture of monocyte-enriched allogeneic leukocytes. In such a method, a mixture of allogenic leukocytes, obtained from least two different, allogeneic donors, is provided. According to an embodiment, two different, allogeneic donors are intended to mean that the two individuals donating leukocytes, are of the same species but of different genetic constitution, i.e. antigenically distinct. As already described, allogenic leukocytes may be obtained from pooled buffy coats or by eluting leukocytes from used leukocyte-depletion filters. Allogeneic monocytes are then isolated from the provided mixture of allogeneic leukocytes. Subsequently, non-exhausted immature DCs are generated from the isolated monocyte-enriched allogeneic leukocytes.

Except for the ability to perform large-scale and cost-effective GMP-enrichment of monocytes, a further advantage of non-exhausted immature DCs, originating from a mixture of allogeneic monocytes derived from at least two different allogeneic donors, is that the normal biological variation as to production of different pro-inflammatory factors upon activation, known to exist between PI-DCs from different donors, will be reduced.

In a preferred embodiment, the allogenic leukocytes are provided by pooling of at least two buffy coats, comprising leukocytes. The buffy coats to be pooled are obtained from at least two different, allogeneic donors. The pooled buffy coats may contain platelets or they may be platelet depleted.

Allogeneic leukocytes may also be provided by eluting leukocytes from at least two leukocyte depletion filters, which filters, respectively, previously have been used to deplete leukocytes from whole blood, from at least two different allogeneic donors. After the elution, the obtained leukocytes are pooled to obtain a mixture of allogeneic leukocytes. Evidently, but less preferred, the whole blood may also be pooled prior to leukocyte depletion. A procedure for eluting leukocytes from a depletion filter, which filter previously has been used to eliminate leukocytes from whole blood, has been described by Ebner et al (cf. Journal of Immunological Methods 252 (2001) 93-104).

Similarly, allogeneic leukocytes may also be provided by eluting leukocytes from a leukocyte depletion filter, which filter has been used to deplete leukocytes from pooled buffy coats, wherein the pooled buffy coats originate from at least two different allogeneic donors. A procedure for eluting leukocytes from a depletion filter, which filter previously has been to eliminate leukocytes from a buffy coat have been described by Meyer et al (cf. Journal of Immunological Methods 307 (2005) 150-166).

While such allogeneic leukocytes, obtained from leukocyte depletion filter, also may be used to produce non-exhausted immature DCs, it seems that is preferred to use allogenic leukocytes provided by pooling of at least two buffy coats, obtained from at least two different, allogeneic donors. Allogenic leukocytes eluted from leukocyte depletion filter, may produce somewhat lower amounts of chemokines, except for MIG, and cytokines, subsequent to maturation, as compared to allogeneic monocytes derived directly from pooled peripheral blood samples or from pooled buffy coats Isolation of monocytes from a mixture of different leukocytes is well-known in the art. According to an embodiment, monocytes are isolated from the provided mixture of allogeneic leukocytes by established GMP-production methods. Thus, monocytes may be isolated from the provided mixture of allogeneic leukocytes by elutriation or by antibody/bead isolation.

Elutriation is a technique wherein continuous counter-flow elutriation separates cells into multiple fractions. In short, a constant centrifugal force that separates the cells by density counters a continuously increasing media flow streaming through the sediment dispersing the cells by size. Hence, smallest/lightest first and biggest/heaviest last, the media flow flushes the cells away into several products.

Antibody/bead isolation of monocytes is performed by (Immuno)-magnetic activated cell sorting (MACS). MACS is a widely employed technique for selective isolation of cells from whole blood, buffy coats, or WBC apheresates. In short, CD-specific antibodies bearing ferro-magnetic beads at their Fc-terminus are coupled to wanted (positive selection) or unwanted (negative selection) cells. Such treated cells may be retained within a porous, metal coated column when exposed to a strong magnetic field.

Subsequent to the isolation, the monocytes are differentiated into immature DCs, i.e. immature DCs are generated. Immature DCs are generated by co-culturing the allogeneic monocytes in an aqueous cell culture medium free from non-human serum and supplemented with granulocyte-macrophage colony stimulating factor (GM-CSF) in combination with interleukin-4 (IL-4), for 2 to 7 days, such as about 5 days, thereby differentiating the monocytes into immature DCs.

As cell culture media comprising fetal calf serum was found to induce premature activation despite being supplemented with GM-CSF and IL-4, it is important that the medium used is free from non-human serum.

Immature DCs may also be generated by culturing the allogeneic monocytes in an aqueous media comprising GM-CSF in combination with interleukin-2 (IL-2), interleukin-15 (IL-15) or interferon alpha for 2 to 7 days, such as 5 days, thereby differentiating the monocytes into immature DCs. Use of GM-CSF in combination with IL-4 is however preferred as it has been shown to prevent alloreactivity and premature activation, when used in combination with a medium free from non-human serum.

The person skilled in the art is familiar with cell culture media and their components. Typically, the cell culture medium used comprises:

at least one salt, such as NaCl, KCl, $MgSO_4$, and/or $Ca(NO_3)_2$;

at least one sugar, such as glucose;

one or several amino acid(s), such as L-methionine, L-phenylalanine, L-proline, L-serine, L-threonine, L-tryptophane, L-tyrosine, L-valine, L-arginine, L-asparagine, L-aspartic, L-cystine, L-glutamine, L-glutamic acid, glycine, L-histidine, L-hydroxyproline, L-isoleucine, L-leucine, and/or L-lysine;

one or several vitamin(s) and other vital nutrient(s), such as glutathione, biotin, vitamin B12, D-Ca-pantothenate, cholin chloride, folic acid, myo-inositol, nictoninamid, p-amino benzoic acid, pyridoxin, riboflavin, and/or thiamine; and at least one buffer, such as phosphate salt (e.g. $Na_2HPO_4$) and/or a carbonate salt (e.g. $NaHCO_3$).

According to an embodiment, the culture medium comprises at least one salt, such as NaCl, at least one sugar, such as glucose, one or several amino acid(s), one or several vitamin(s), and a buffer, such as phosphate salt (e.g. $Na_2HPO_4$) and/or a carbonate salt (e.g. $NaHCO_3$).

Further, while the cell culture medium further is free from non-human serum it typically comprises at least human polypeptide. According to an embodiment, the cell culture medium comprises at least one human polypeptide selected from the group consisting of transferrin, albumin, and insulin; preferably the cell culture medium comprises all three of them. The human polypeptide may be obtained from human plasma. Further they may be recombinantly produced. As an example insulin may be recombinantly produced in yeast cells.

As an example, the cell culture medium free from non-human serum may be CellGro®, which is a GMP serum-free dendritic dell medium (DC) provided by CellGenix GmbH. In the US the medium is sold under the trademark CellGenix™.

As recognized by the skilled person and as explained herein, the term isolated does not necessarily refer to 100% purity, but to monocytes obtained by an isolation process showing preference for monocytes. Monocytes obtained by such a process may be referred to as monocyte-enriched allogeneic leukocytes, as other leukocytes in addition to monocytes will be present.

According to an embodiment, the allogeneic monocytes are enriched from the mixture of allogeneic leukocytes. Monocyte-enriched allogeneic leukocytes in addition to monocytes typically also comprise allogeneic neutrophils. Further, they may comprise other granulocytes.

In contrast to the prevailing prejudice, no signs of premature activation was seen, when the allogenic monocytes were co-cultured in aqueous cell culture medium free from non-human serum and supplemented with GM-CSF/IL-4, despite that fact that immature DC s were obtained from a mixture of allogeneic leukocytes. Accordingly, such immature DCs are non-exhausted, thus being able to produce substantial amounts, such as more than 2 000, 5 000, or 7 500 pg/mL, of pro-inflammatory chemokines, including MIP-1 alpha, MIP-1 beta, RANTES and MIG, and substantial amounts, such as more than 500, 1 500 or 3 000 pg/mL, of pro-inflammatory cytokines, including IL-12p70 and TNF-alpha in a sustained fashion subsequent to withdrawal of the activating factors.

According to an embodiment, immature is intended to mean DCs which express only low levels of the DC maturation markers CD83 and CD86 and which are able to produce high amounts of proinflammatory chemokines and cytokines upon activation. Low levels are, according to embodiment, to be interpreted such that an at least 3-fold, such as at least 5-fold, increase in the CD83-expression is seen upon activation, and that an at least 5-fold, such as at least 8-fold, increase in the CD86-expression is seen upon activation.

As it was envisaged that premature activation was to be seen, the cycloxoygenase-2 inhibitor NS-398, a factor known to hamper prostaglandin E2 (PGE2)-mediated exhaustion of activated DCs was added in some experiments. However, the presence of NS-398 during propagation of monocytes into DCs did not increase, but rather decrease, the activation-induced production of MIG and IL-12p70. Thus, there are no signs of PGE2-mediated exhaustion of differentiated immature DCs from co-cultures of mixed allogeneic monocytes.

As recognized by the skilled person (cf. e.g. EP 1 509 244 B1 and WO 2011/098516), non-exhausted immature dendritic cells (DCs) are useful in the production of pharmaceutical composition for the treatment of cancer. Thus, an embodiment relates to a mixture of allogeneic non-exhausted immature dendritic cells (DCs) originating from at least two different, allogeneic donors. Such dendritic cells (DCs) are obtainable by such a method as disclosed herein. Subsequent to the differentiation into immature DCs, the immature DCs may be activated to become pro-inflammatory DCs. Activation may be induced in several ways. Many signals have been shown to induce at least some aspects of DC activation. Among the most powerful of these are microbial and viral products (pathogen-associated molecular patterns (PAMPs), which are directly recognized by pattern-recognition receptors (PRRs), including members of the Toll-like receptor (TLR) family. PRRs control the expression of many innate response genes and can directly signal for DC activation. In addition, PRR signaling in both immune and non-immune cells often leads to the synthesis of inflammatory cytokines, such as tumor necrosis factor (TNF) and interleukin 1 (IL-1), which can also promote DC activation. Thus, addition of inflammatory cytokines may also contribute to the activation of immature DCs.

According to an embodiment, the immature DCs are loaded with antigens prior to, or simultaneous with, the activation, in order to provide a cellular allogeneic anti-cancer vaccine. Antigen-loading is well-known in the art (cf. e.g. EP 1 509 244 B1) and may performed with methods, such as pulsing, transfection, infection or fusion. As an example, the antigen may typically be obtained from a tumor; typically the tumor type which the vaccine is to be directed to. In obtaining antigens, a representative specimen of cancer type of interest typically is used.

According to a preferred embodiment, the activation of the immature DCs is performed in accordance with the method disclosed in WO 2011/098516. Maturation may thus be induced by adding the Toll-like receptor 3 (TLR3)-ligand poly-I:C, a TLR7/8-ligand, such as R848 (Resiquimod) and the cytokine interferon gamma (IFN-γ). The Toll-like receptor 3 (TLR3)-ligand poly-I:C is a synthetic analog of dsRNA comprising a strand of poly(I) annealed to a strand of poly(C). The size of the strand may vary. The size may be 200 base pairs to 8 000 base pairs, such 200 to 1 500 or 1 500 to 8 000 base pairs. The TLR7/8-ligand R848 is also denoted Resiquimod in the art. As an alternative to Resiquimod, Gardiquimod or Imiquimod may be used as TLR7/8-ligands. Typically, the immature DCs are exposed to the activation factors for 8 to 24 hours, such as 18 hours.

The activation may further include the addition of at least one substance selected from the group consisting of TLR2-ligands, TLR4-ligands, such as bacterial lipopolysaccharide and monophosphoryl lipid A, TLR9-ligands, such as CpG oligonucleotides (ODN) sequences that distinguish microbial DNA from mammalian DNA, Interferon alpha (IFN-α), interleukin 1β (IL-1β), and tumor necrosis factor alpha (TNF-α). Further, the activation does preferably not comprise addition of prostaglandin E2 (PGE2) in order to prevent the mature DCs from becoming migratory DCs that rapidly will leave the injection site (tumor), which would be disadvantageous within the context of this invention.

Subsequent to the activation, the resulting pro-inflammatory DCs may be washed to remove essentially all of the activation factors. Thus, the activation factors typically are washed away prior to use of the pro-inflammatory DCs as vaccine. Removal of the activation factors avoids co-administration of activation factors (aimed to induce pro-inflammatory DCs ex vivo). Co-administration of activation factors most likely will lead to a strong and persistent activation also of intratumorally recruited immature DCs, leading to their differentiation into pro-inflammatory mature DCs rather than the desired differentiation into migratory mature DCs.

As already described (cf. WO 2011/098516), pro-inflammatory dendritic cells are useful in the treatment of cancer, as they may activate a patient's own DCs to develop into tumor-loaded migratory DCs. An embodiment, thus relates to mixture of allogeneic pro-inflammatory dendritic cells originating from at least two different, allogeneic donors. Such allogeneic pro-inflammatory dendritic cells are obtainable by such a method as disclosed herein. By freezing the pro-inflammatory dendritic cells subsequent to the activation they may be stored. Typically the pro-inflammatory dendritic cells are frozen in a medium containing dimethylsulphoxide (DMSO) and serum or plasma. Before use, the frozen cells are thawed and the DMSO is washed away.

For use in the treatment of cancer, such allogeneic pro-inflammatory dendritic cells may be formulated into a pharmaceutical composition. The pharmaceutical composition may comprise at least one pharmaceutical acceptable carrier, such as a phosphate buffered saline solution, water, and emulsions, such as an oil/water or water/oil emulsion, and various types of wetting agents. Further, it may comprise pharmaceutical acceptable adjuvants, excipients, stabilizers preservatives and/or other components known in the art. As an example, the carrier may be a saline solution comprising human serum albumin.

A further embodiment relates to such a mixture of allogeneic pro-inflammatory dendritic cells, or such a composition comprising such allogeneic pro-inflammatory dendritic cells, for use in the treatment of cancer. Similarly, an embodiment relates to use of such a mixture of allogeneic pro-inflammatory dendritic cells for use in the manufacture of a medicament for the treatment of cancer. A further embodiment relates to a method of treating cancer, wherein a mixture of allogeneic pro-inflammatory dendritic cells is administrated to a patient in need of such treatment in dose sufficient to activate the patient's own DCs to develop into tumor-loaded migratory DCs.

Without further elaboration, it is believed that one skilled in the art can, using the preceding description and the following experimental part, utilize the present invention to its fullest extent. The preferred specific embodiments described herein are, therefore, to be construed as merely illustrative and not limitative of the remainder of the description in any way whatsoever. Further, although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc. do not preclude a plurality.

EXPERIMENTAL

Figure 1A:
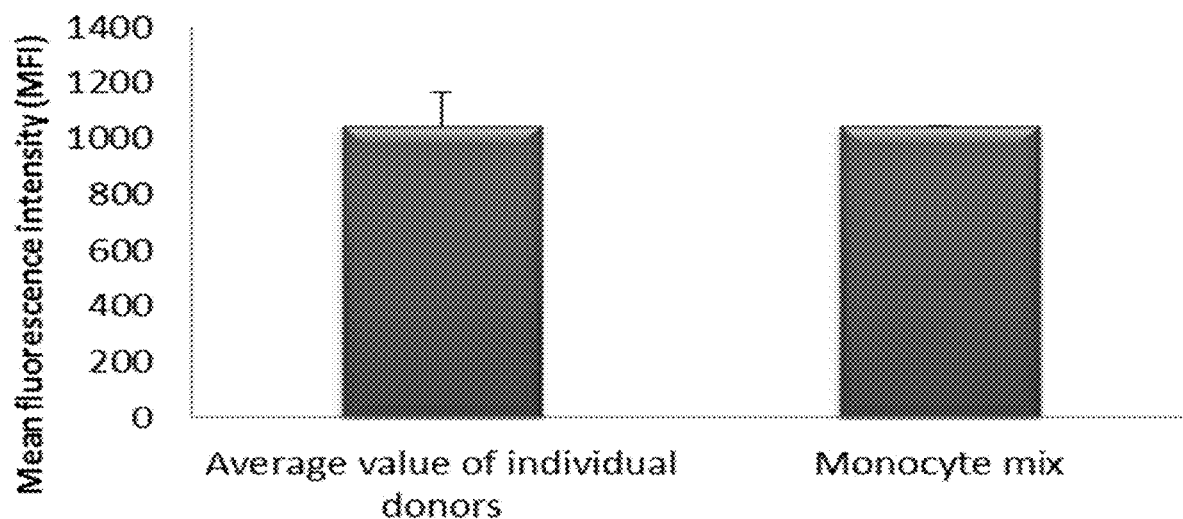
FIG. 1A illustrates the expression of the activation/maturation marker CD83 on immature DCs derived from single or mixed peripheral blood monocyte cultures.

The following examples are mere examples and should by no means be interpreted to limit the scope of the invention. Rather, the invention is limited only by the accompanying claims.

Leukocyte of Various Origin

Isolation of Leukocytes from Leukocyte Depletion Filters (TACSI Filters)

Leukocyte filters (TACSI leukocyte depletion filters used for routine leukocyte depletion of 4 pooled buffy coats during platelet production) were collected at the Component Laboratory at the Department of Transfusion Medicine, Sahlgrenska University Hospital, Gothenburg, and transported to the laboratory (Department of Clinical Immunology, Sahlgrenska University Hospital) on ice.

In the laboratory, a Syringe (Terumo®) was filled with 50 ml of PBS/EDTA buffer (CliniMACS®) and connected to the TACSI® filter through a luer-lock fitting. The filter was back-flushed into a sterile glass flask, three times (150 ml PBS/EDTA buffer in total). The eluted cell suspension was finally diluted with PBS (PAA, Fisher Scientific) at a 1:2 concentration in a Falcon™ tube (Fisher® brand, Fisher Scientific).

Buffy Coats

Buffy coats from healthy blood donors were collected at the department of Transfusion Medicine and transported to the laboratory at room temperature.

Peripheral Blood

Peripheral blood from healthy donors was collected at the department of Transfusion Medicine and transported to the laboratory at room temperature. In the laboratory, the blood was mixed with room temperature PBS at a 1:2 concentration in a Falcon™ tube.

Isolation of Peripheral Blood Mononuclear Cells (PBMC)

Peripheral blood from healthy donors was collected at the department of Transfusion Medicine and transported to the laboratory at room temperature. In the laboratory, the blood was mixed with room temperature PBS at a 1:2 concentration in a Falcon™ tube. The cell suspension was gently transferred to 10 ml centrifuge tubes (Nunc) containing 3 ml of Lymphoprep™ (Axis-Shield). 5-6 ml was transferred to each tube followed by centrifugation at 2000 rpm, 20 min at room temperature and without brake. The isolated PBMCs were transferred to pre-cooled 10 ml tubes. The cells were washed twice by filling the tubes with cold PBS followed by centrifugation at 1450 rpm, 10 minutes at 4° C. The supernatants were discarded and the pellets were re-suspended in 1 ml of cold PBS. Another 9 ml of was added to each tube.

Monocyte Isolation 5 mL fractions of eluted filter leukocytes/buffy coat leukocytes or isolated PBMCs from 10-20 mL of whole peripheral blood were centrifuged in tubes at 1450 rpm, 10 minutes at 4° C. The supernatants were completely removed and the cell pellets were re-suspended in 80 μl of PBS/EDTA (Miltenyi) per $10^7$ cells. 20 µl of CD14 microbeads (Miltenyi) was added per $10^7$ cells. The cells were mixed and incubated for 15 minutes at 4° C. and subsequently washed by adding 1-2 ml of PBS/EDTA followed by centrifugation at 300×g for 10 minutes. The supernatants were completely removed and remaining cells were re-suspended in 500 µl of PBS/EDTA.

MidiMACS™ separators (Miltenyi) were placed in a magnetic multistand (Miltenyi) and rinsed with 3 ml of PBS/EDTA. The cell suspensions were placed onto the MidiMACS™ separators allowing the cells to pass through. The MidiMACS™ separators were washed three times with 3 ml of PBS/EDTA. The effluent fractions with unlabeled cells were discarded. The MidiMACS™ separators were removed from the magnetic multistand and placed onto a Falcon tube. 5 ml of PBS/EDTA buffer was pipetted onto the column and the cells were immediately pushed through with a plunger.

Cell concentration was determined in a Bürker chamber. The cell suspensions containing monocytes were centrifuged at 1450 rpm, 10 minutes at 4° C. The supernatants were discarded and the cells were re-suspended in CellGro® DC-media (CellGenix). The purity of CD14+ monocytes within all monocyte-isolated cell cultures was >80%, as determined by FACS-analysis, see below.

Generation of Immature DCs

The leukocytes originating from the TACSI filters were re-suspended to the concentration of 300 000 cells/mL in CellGro® DC-media, being a medium free from non-human serum, and plated in 24-well plates (1 mL per well). Monocyte-enriched leukocytes from buffy coats and peripheral blood were first re-suspended to a concentration of $5 \times 10^5$ monocytes/mL in CellGro® media. 400 µl of CellGro® media (without cells) was first added to 12 wells (A1-6, B1-3, C1-3) in a 24-well plate. 600 µl of the monocyte-enriched cell suspension from donor A (buffy coat or peripheral blood respectively) was transferred to well A1-3. 600 µl of monocyte-enriched cell suspension from donor B (buffy coat or peripheral blood) was transferred to well B1-3. 600 µl of the monocyte-enriched cell suspension from donor C was transferred to well C1-3 (buffy coat or peripheral blood). In well A4-6, 200 µl of monocyte-enriched cell suspension was transferred from all three donors (buffy coat or peripheral blood). The final cell number in all wells was 300,000 cells (in a volume of 1 mL CellGro® media per well).

In order to differentiate the monocytes into immature DCs, the culture medium was supplemented with 1000 U/mL recombinant human IL-4 and 1000 U/mL recombinant human GM-CSF (all from CellGenix, Freiburg, Germany) and cells were subsequently cultured for 5 days.

Activation/Maturation of Immature DCs

Following 5 days of culture in CellGro® medium supplemented with IL-4 and GM-CSF, activation/maturation of the immature DCs was induced by adding 20 µg/mL polyI:C (Sigma, Steinheim, Germany), an immunostimulant specific to the TLR-3 receptor also known as polyinosinic:polycytidylic acid or polyinosinic-polycytidylicf acid sodium salt, 2.5 µg/mL R848 (Sigma, Steinheim, Germany), toll-like receptor 7/8-ligand also known as resiquimod, and 1000 U/ml interferon gamma (IFN-γ, R&D systems, Minneapolis, USA). After 18 h of incubation, the cells were washed three times and further incubated in fresh AIM-V® medium (without addition of exogenous activating factors) for 24 h Culture supernatants from the cultures were harvested according to protocols well known to a person skilled in the art.

ELISA analysis was performed on the supernatants as described below, in order to analysis the levels of pro-inflammatory chemokines and the pro-inflammatory cytokines Evaluation of the Levels of Pro-Inflammatory Chemokines and the Pro-Inflammatory Cytokines by ELISA The pro-inflammatory chemokines CCL3/MIP-1α, CCL4/MIP-1β, CCL5/RANTES and CXCL9/MIG and the pro-inflammatory cytokines IL-12p70 and TNF-α were measured by enzyme-linked immune adsorbent assay (ELISA) using Duo Set ELISA Development System from R&D systems, Minneapolis, USA according to the manufacturer's instructions.

Phenotypic Examination by Flow Cytometry

Monocytes and monocyte-derived DCs were generated as described above. The frequency of CD14+ monocytes after monocyte isolation was estimated by staining cells with FITC-anti human CD14. After 5 days of incubation in CellGro® supplemented with IL-4 and GM-CSF, the immature DCs were washed and subsequently stained with PE anti-human CD86 in combination with FITC anti-human CD83. Immature DCs that subsequently had been activated for 18 hours with activating factors were also stained with PE anti-human CD86 in combination with FITC anti-human CD83. Mouse IgG1 and IgG2 stained with FITC and PE were used as isotype controls (all from BD Biosciences, California, USA). The samples were analyzed by flow cytometry (FACS) using CellQuest™ software (BD Bioscience, California, USA).

Results

Below, the results from the experimental part are commented.

DCs Derived from Co-Cultures of Monocyte-Enriched Allogeneic Leukocytes are not Phenotypically Activated/Mature when Co-Cultured in Aqueous Cell Culture Medium Free from Non-Human Serum and Supplemented with GM-CSF and IL-4

Figure 1B:
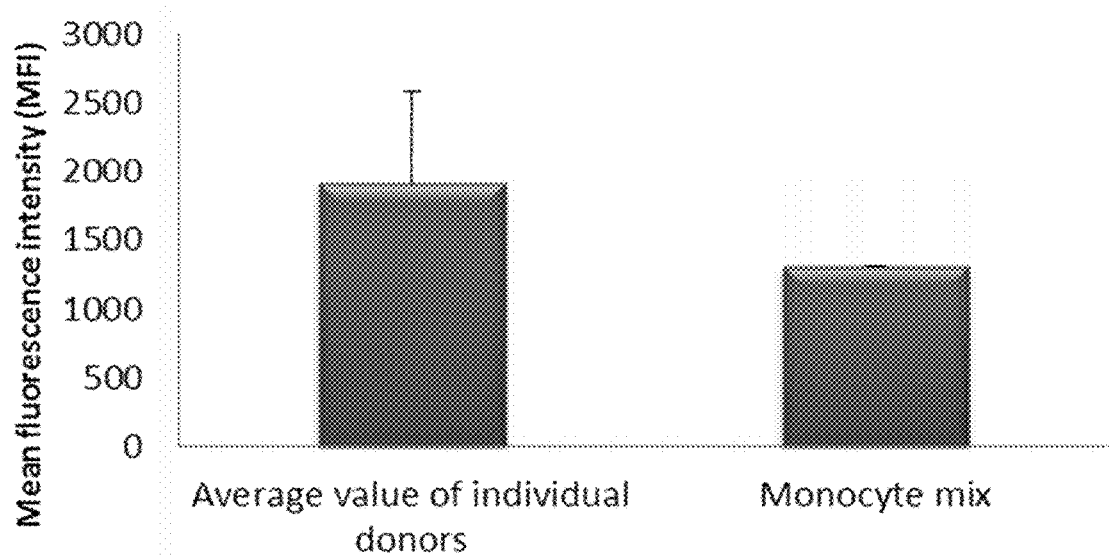
FIG. 1B illustrates the expression of the activation/maturation marker CD86 on immature DCs derived from single or mixed peripheral blood monocyte cultures.
Figure 1C:
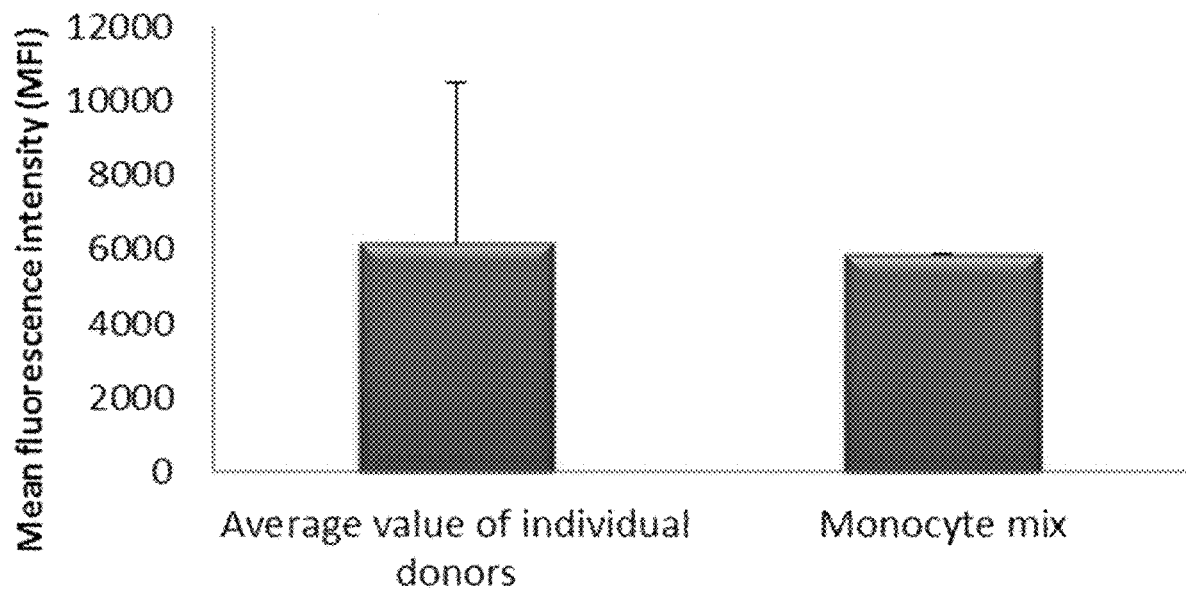
FIG. 1C illustrates the expression of the activation/maturation marker CD83 on PI-DCs derived from single or mixed peripheral blood monocyte cultures.
Figure 1D:
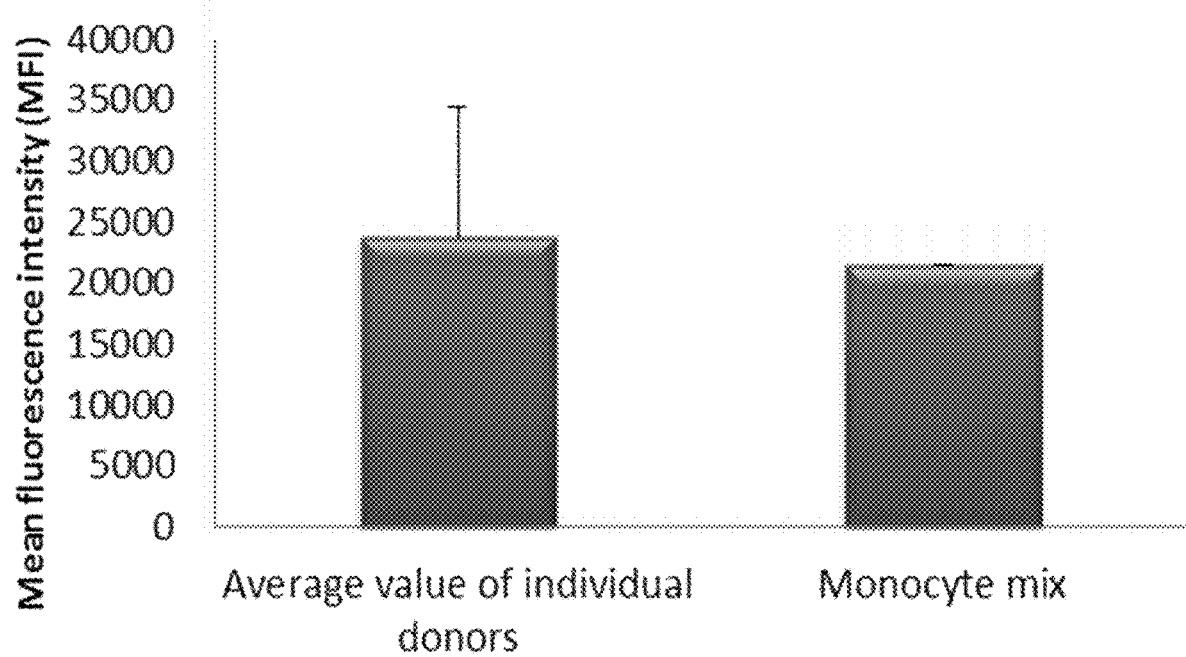
FIG. 1D illustrates the expression of the activation/maturation marker CD86 on PI-DCs derived from single or mixed peripheral blood monocyte cultures.
Figure 2A:
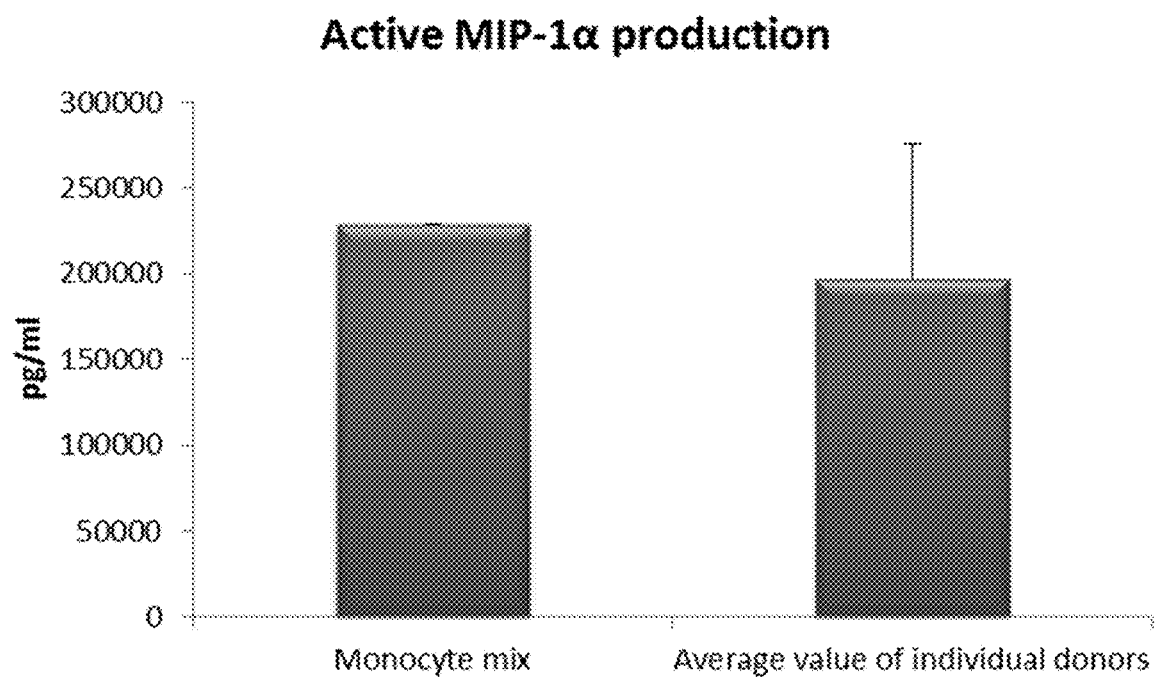
FIGS. 2A, 2B, 2C and 2D illustrate pro-inflammatory chemokine production by immature DCs (derived from single or mixed peripheral blood monocyte cultures) during 18 hours of persistent stimulation with activating factors ("Active production").
Figure 2B:
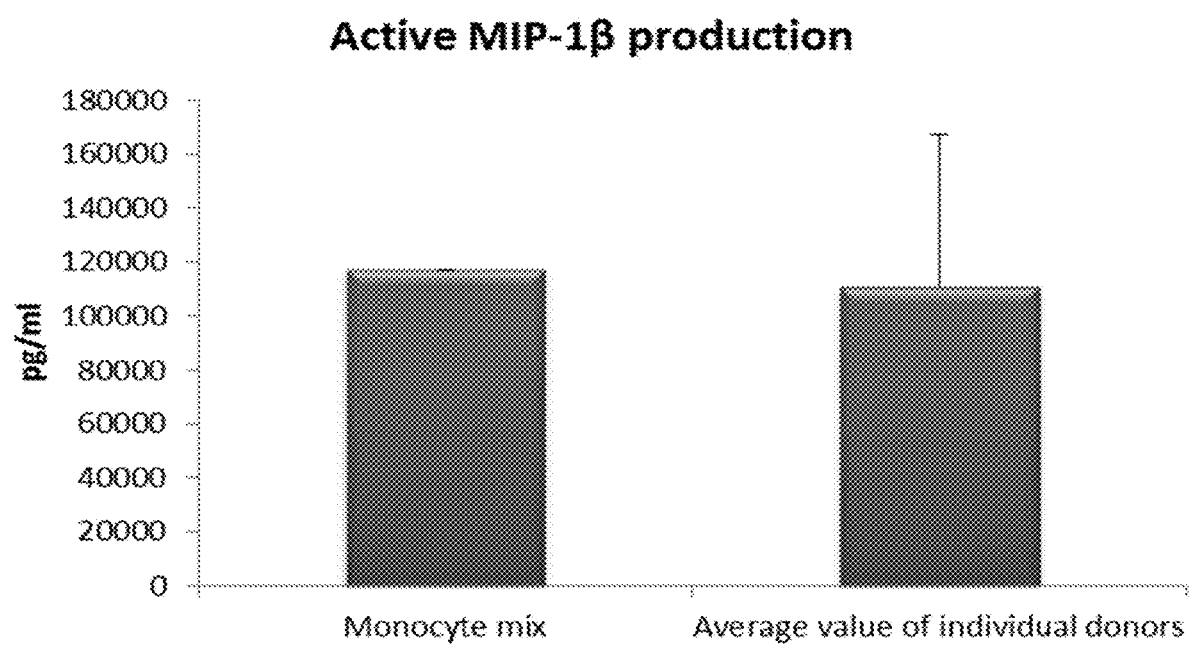
Figure 2C:
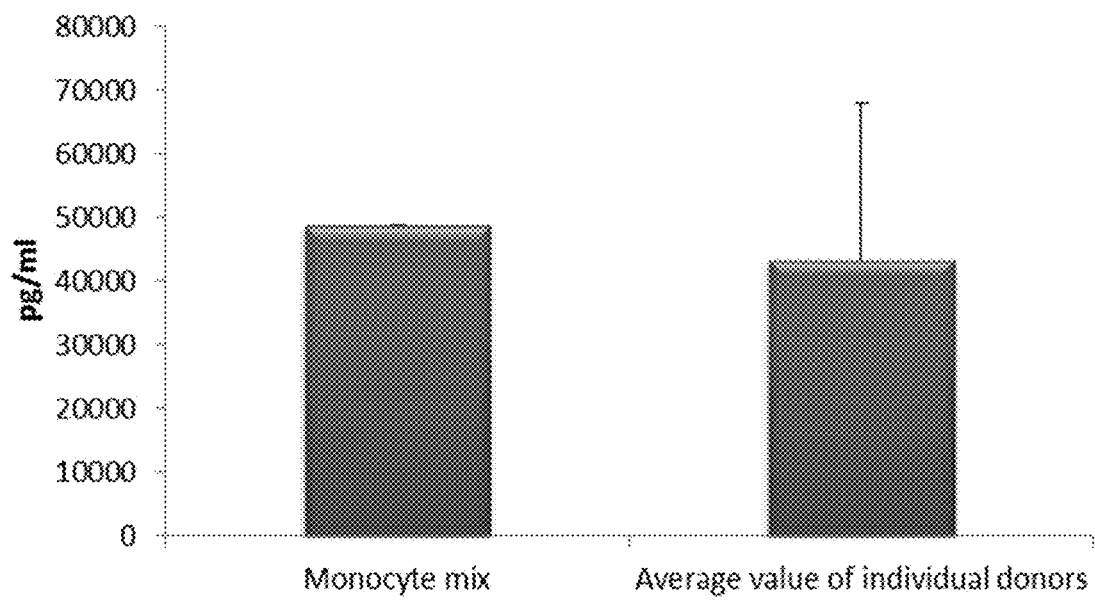
Figure 2D:
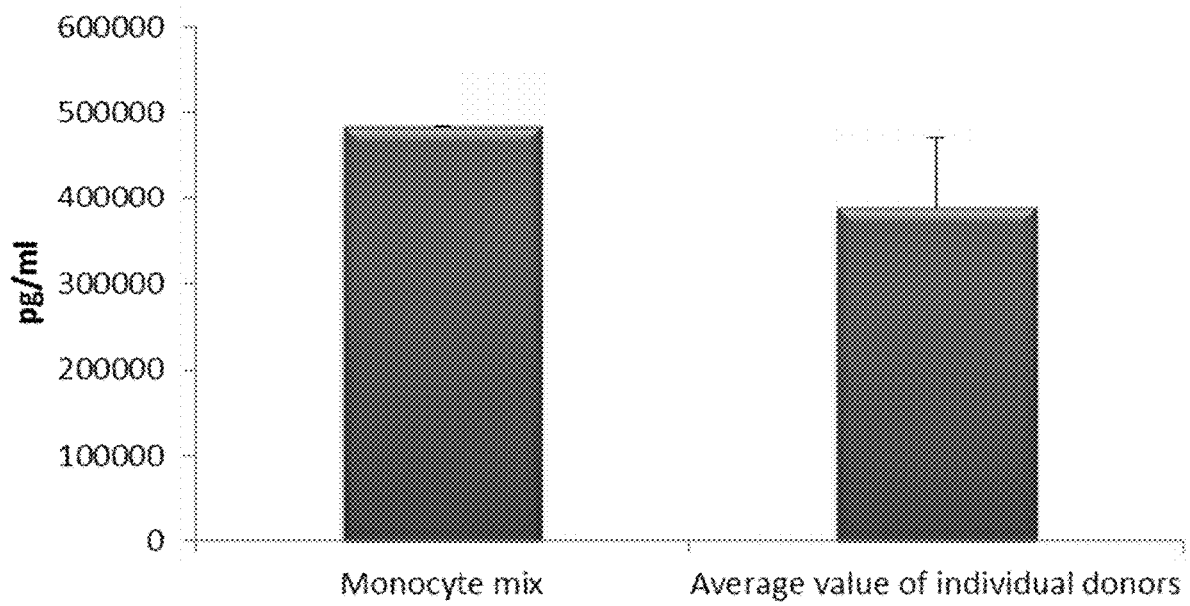

Propagation of monocytes from single blood donors in cell culture medium free from non-human serum and supplemented with GM-CSF and IL-4 for 4-7 days give rise to non-exhausted DCs with a typical "immature" phenotype, including low expression of the maturation marker CD83 and low expression of the costimulatory molecule CD86. As seen in FIGS. 1A and B, the mean-expression of both CD83 and CD86 for 3 different "single" DCs was similar as compared to CD83 (FIG. 1A) and CD86 (FIG. 1B) expression of DCs derived from a mixture of all three donors. As seen in FIGS. 1C and D, the strongly increased mean-expression of the activation/maturation markers CD83 and CD86 for "single" DCs (DCs from 3 different peripheral blood donors analysed) after propagation in aqueous cell culture medium free from non-human serum and supplemented with GM-CSF and IL-4 for 4 days and subsequent persistent activation with stimulating factors for 18 hours was similar as compared to CD83 (FIG. 1C) and CD86 (FIG. 1D) expression on activated DCs derived from a mixture of allogeneic monocyte-enriched leukocytes from all three donors.

Taken together, these findings indicate that monocyte-derived DCs from the mixed allogeneic monocyte population are immature after culture in GM-CSF and IL-4 for 5 days and have therefore not experienced any activation/maturation signals during their differentiation from monocytes into immature DCs. Moreover, immature DCs from the mixed allogeneic monocyte-population are at least phenotypically non-exhausted as they strongly respond with phenotypic maturation when stimulated with activating factors.

Data obtained with flow cytometry. The respective Y-axis shows the mean fluorescence intensity (MFI) for CD83 and CD86 before and after persistent stimulation with activating factors for 18 hours. The X-axis show the different combinations measured.

Immature DCs Derived from Co-Cultures of Mixed Allogeneic Peripheral Blood Monocytes are not Functionally Exhausted.

Propagation of monocytes (from one single blood donor) in culture medium supplemented GM-CSF and IL-4 for 4-7 days is known to give rise to non-exhausted DCs which respond with a vigorous production of pro-inflammatory chemokines (MIP-1 alpha, MIP-1 beta, RANTES and MIG) and pro-inflammatory cytokines (IL-12p70 and TNF-alpha) upon stimulation with certain activating factors.

Figure 3A:
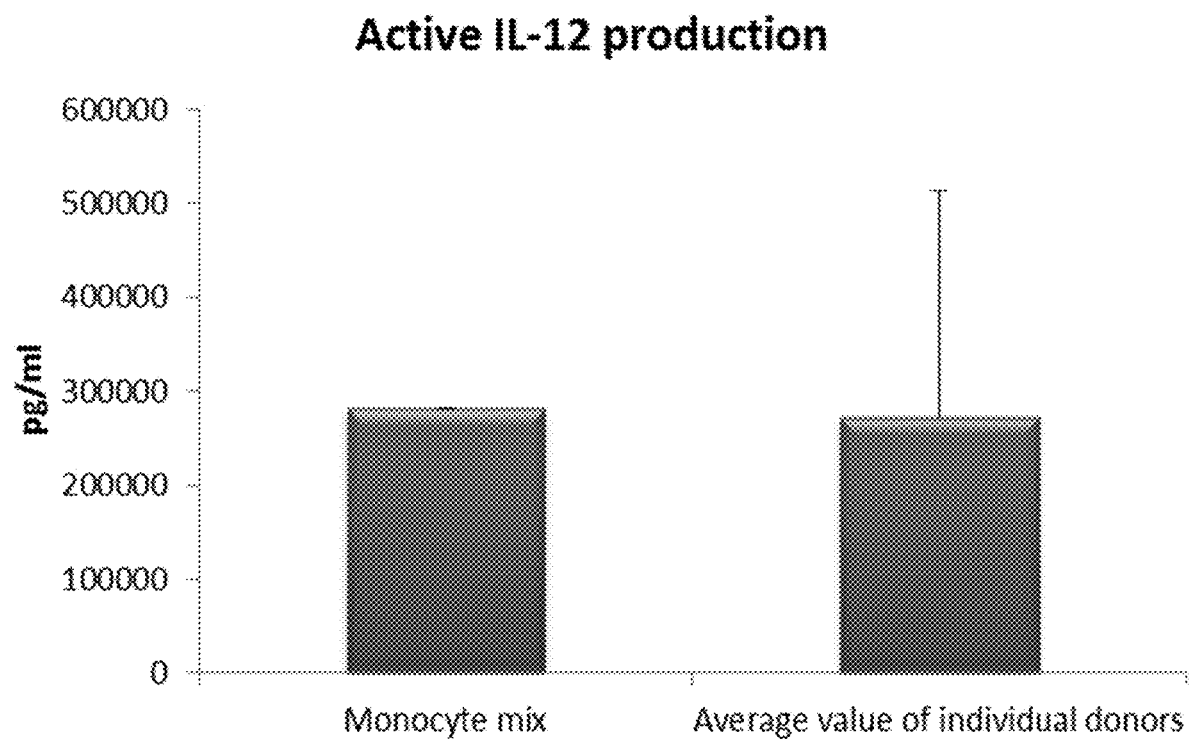
FIGS. 3A and 3B illustrate pro-inflammatory cytokine production by immature DCs (derived from single or mixed peripheral blood monocyte cultures) during 18 hours of persistent stimulation with activating factors ("Active production").
Figure 3B:
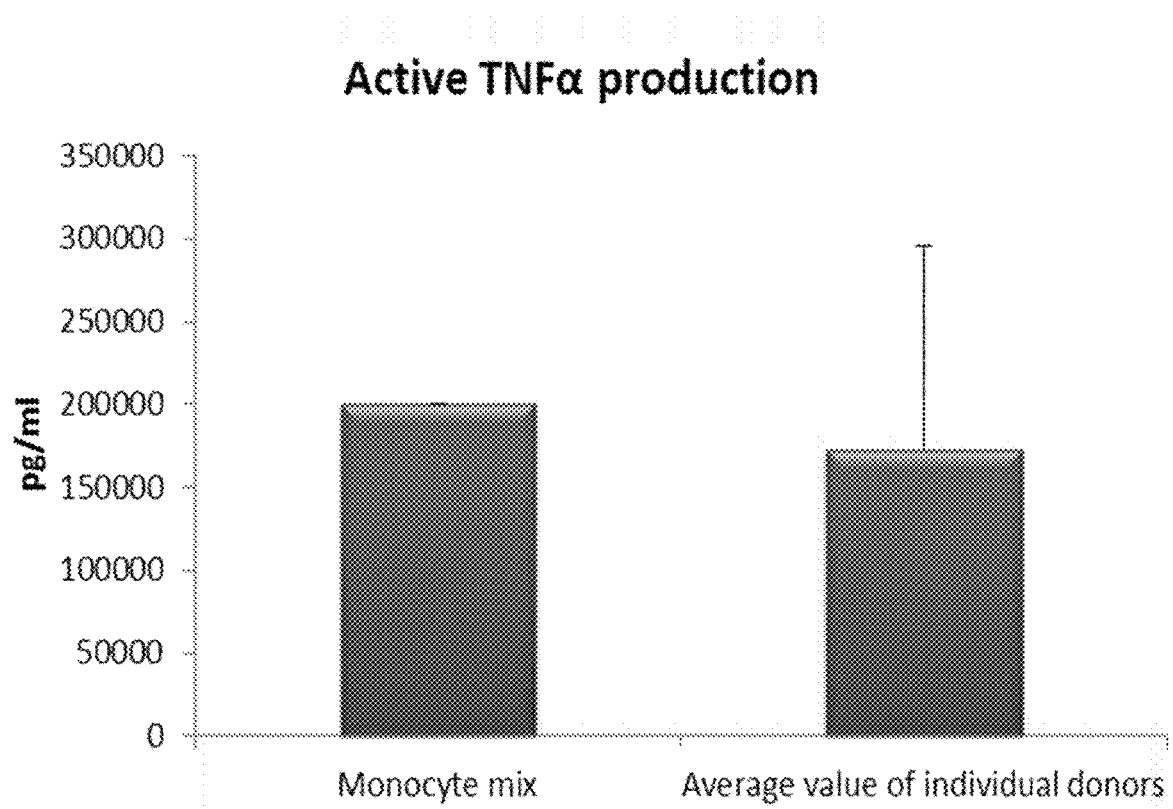
Figure 4A:
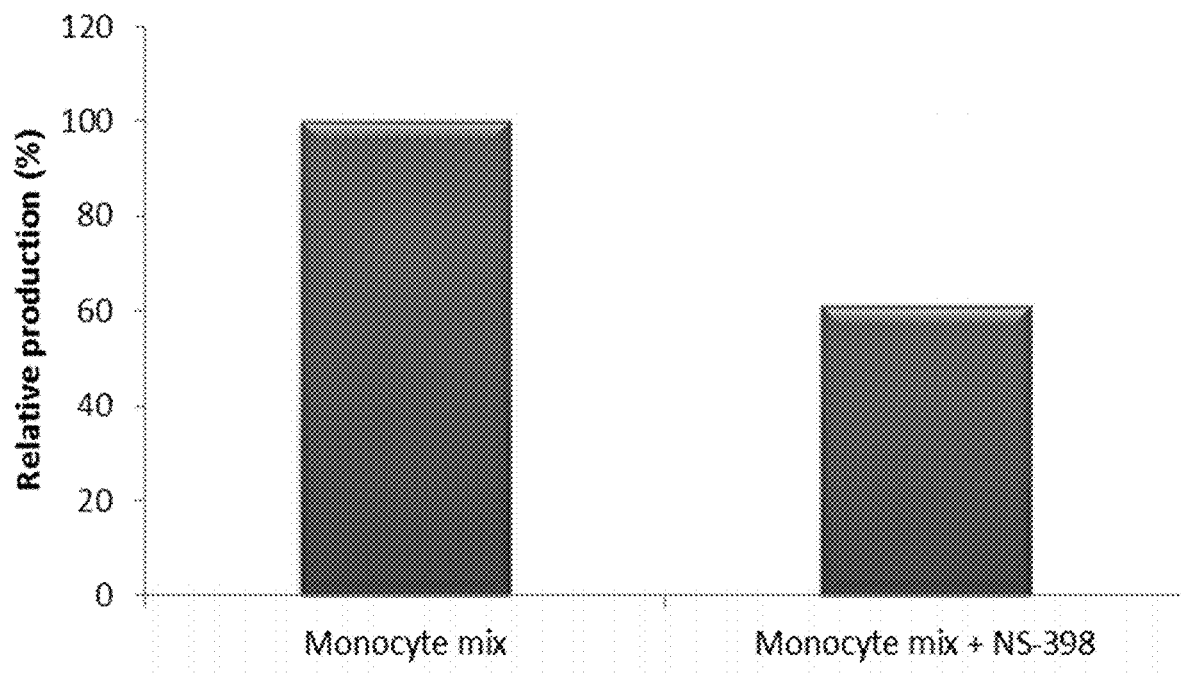
FIGS. 4A and 4B illustrate pro-inflammatory cytokine production by immature DCs (derived from single or mixed peripheral blood monocyte cultures) during 18 hours of persistent stimulation with activating factors +/− addition of the cycloogygenase-2 (Cox-2) inhibitor NS-398.
Figure 4B:
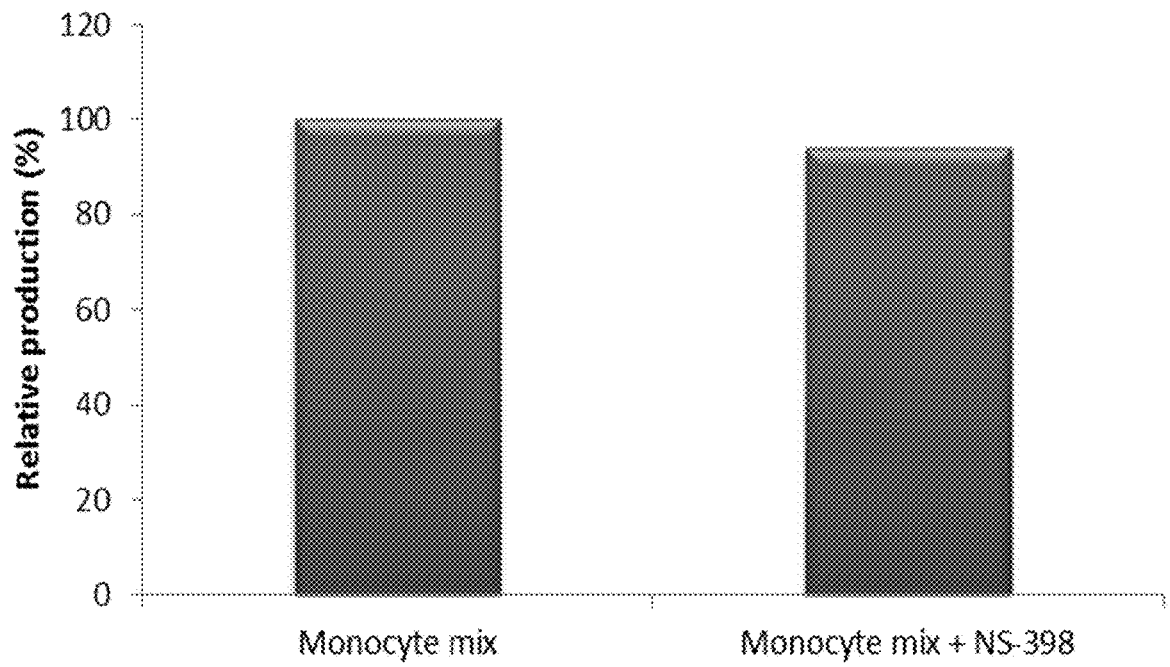
Figure 5A:
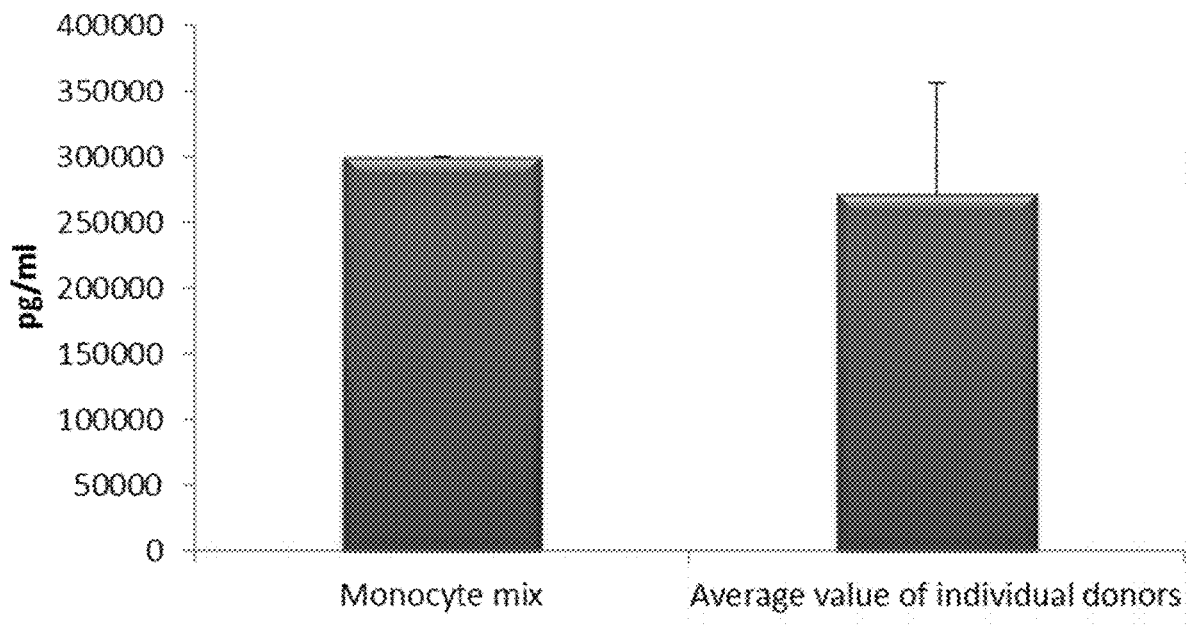
FIGS. 5A, 5B, 5C, and 5D illustrate pro-inflammatory chemokine production by immature DCs (derived from single or mixed buffy coat monocyte cultures) during 18 hours of persistent stimulation with activating factors ("Active production").
Figure 5B:
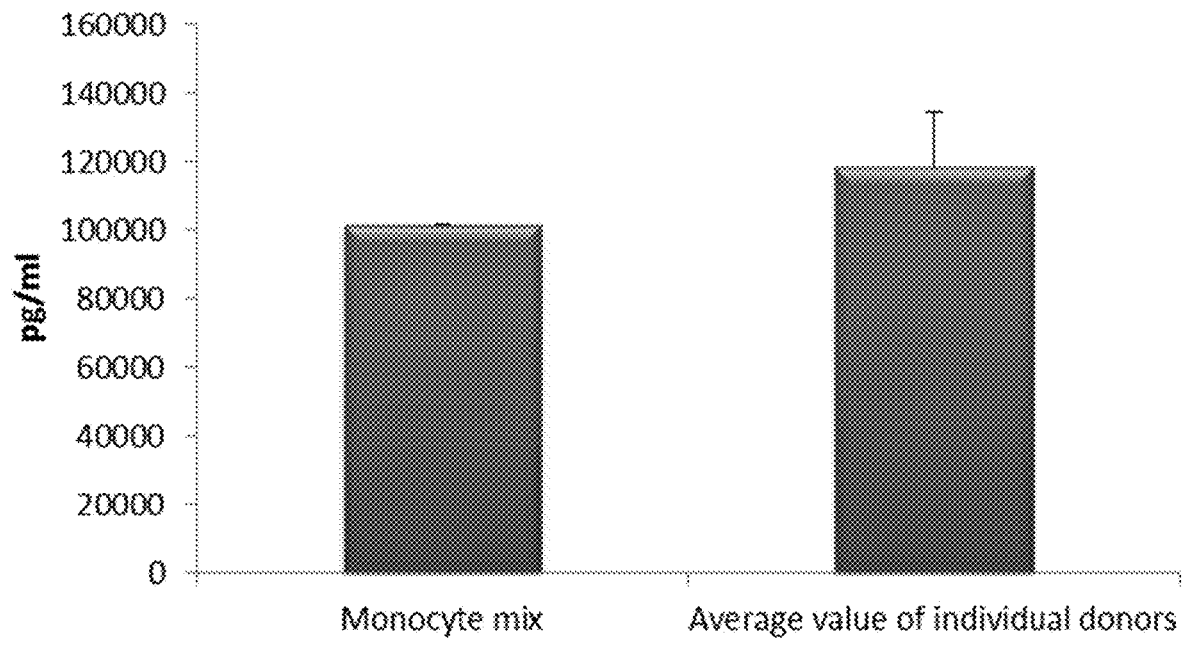
Figure 5C:
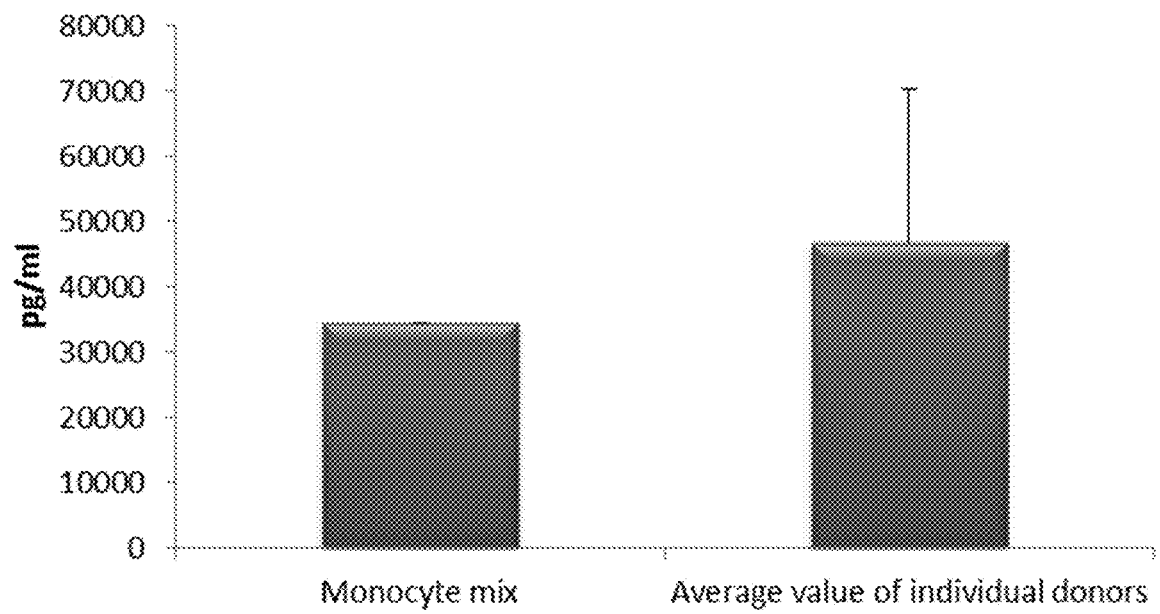
Figure 5D:
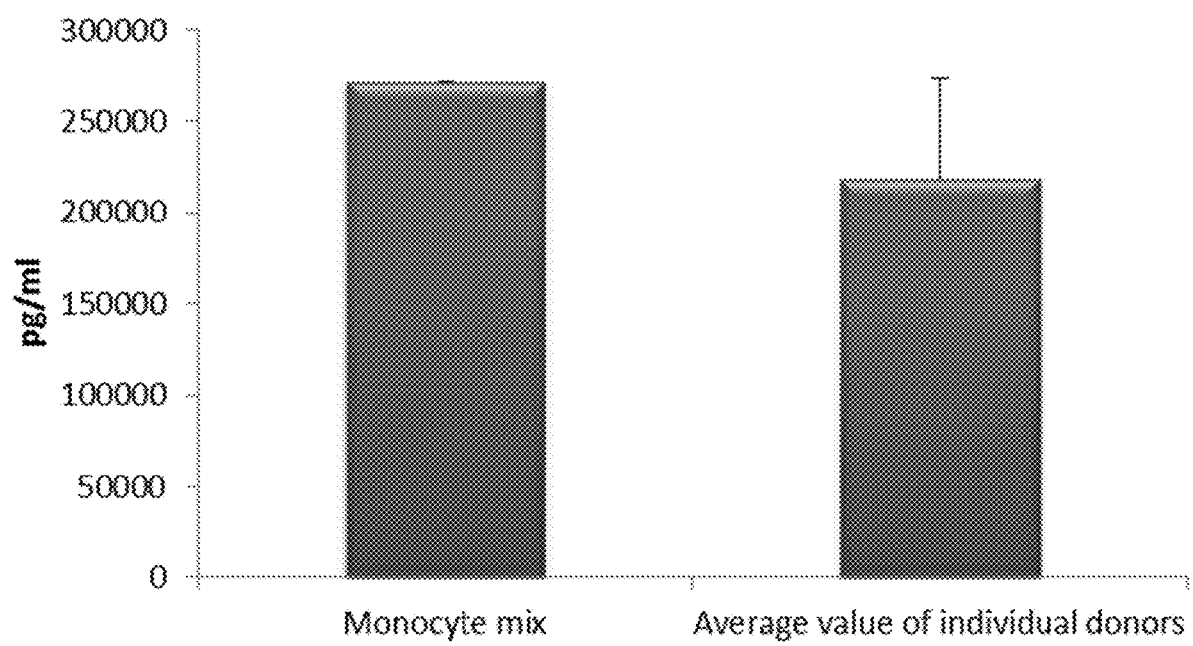

As seen in FIG. 2, the high mean levels of MIP-1 alpha (FIG. 2A), MIP-1 beta (FIG. 2B), RANTES (FIG. 2C), MIG (FIG. 2D) produced by "single" DCs (DCs from three different peripheral blood donors analysed) during persistent activation with stimulating factors for 18 hours was similar as compared to DCs derived from a mixture of monocytes from all three donors. Notably, there is a substantial variation in activation-induced chemokine production between different single donor DCs. As seen in FIG. 4, the high mean levels of IL-12p70 (FIG. 3A) and TNF-alpha (FIG. 3B) produced by activated "single" DCs was similar as compared to DCs derived from a mixture of monocytes from of all three donors. Notably, there is a substantial variation in IL-12p70 and TNF-alpha production between different single-donor DCs Data were obtained from ELISA analysis. Results shown are mean values±SD from three individuals and the value obtained from the mixture of all three donors. The respective Y-axis shows the amount of the respective substance produced in pg/mL/$1\times10^6$ cells, during 18 hours of persistent stimulation/activation. The X-axis show the different combinations measured.

Prostaglandin E2 (PGE2) has been suggested to play a central role in activation-induced exhaustion of immature DCs (Rieser C. et al., Differential Deactivation of Human Dendritic Cells by Endotoxin Desensitization: Role of Tumor Necrosis Factor-α and Prostaglandin E2. Blood 91 (1998) 3112-3117). We therefore investigated if addition of the Cox-2 inhibitor NS-398 (aimed to inhibit potential production of PGE2) during co-cultivation of allogeneic monocytes would increase the production of proinflammatory chemokines (represented by MIG-production) or proinflammatory cytokines (represented by IL-12p70 production) upon subsequent activation. As seen in FIG. 4, the presence of the Cox-2 inhibitor NS-398 during propagation of monocytes into DCs did not increase, but rather decreased, the activation-induced production of MIG and IL-12p70. Thus, there are no signs of PGE2-mediated exhaustion of differentiated immature DCs from co-cultures of mixed allogeneic monocytes.

Data were obtained from ELISA analysis. Results shown are from one experiment from the mixture of all three donors. The respective Y-axis shows the amount of the respective substance produced in pg/mL/$1\times10^6$ cells, during 18 hours of persistent stimulation/activation. The X-axis show the different combinations measured.

Immature DCs Derived from Co-Cultures of Mixed Allogeneic Monocyte-Enriched Buffy Coat Leukocytes are not Functionally Exhausted.

As seen in FIG. 5, the high mean levels of the activation-induced pro-inflammatory chemokines MIP-1 alpha (FIG. 5A), MIP-1 beta (FIG. 5B), RANTES (FIG. 5C), MIG (FIG. 5D) produced by "single" DCs (DCs from three different buffy coat donors analysed) during persistent activation with stimulating factors for 18 hours was similar as compared to DCs derived from a mixture of monocytes from all three donors. Notably, there is a substantial variation in chemokine production between different single donor DCs.

Figure 6A:
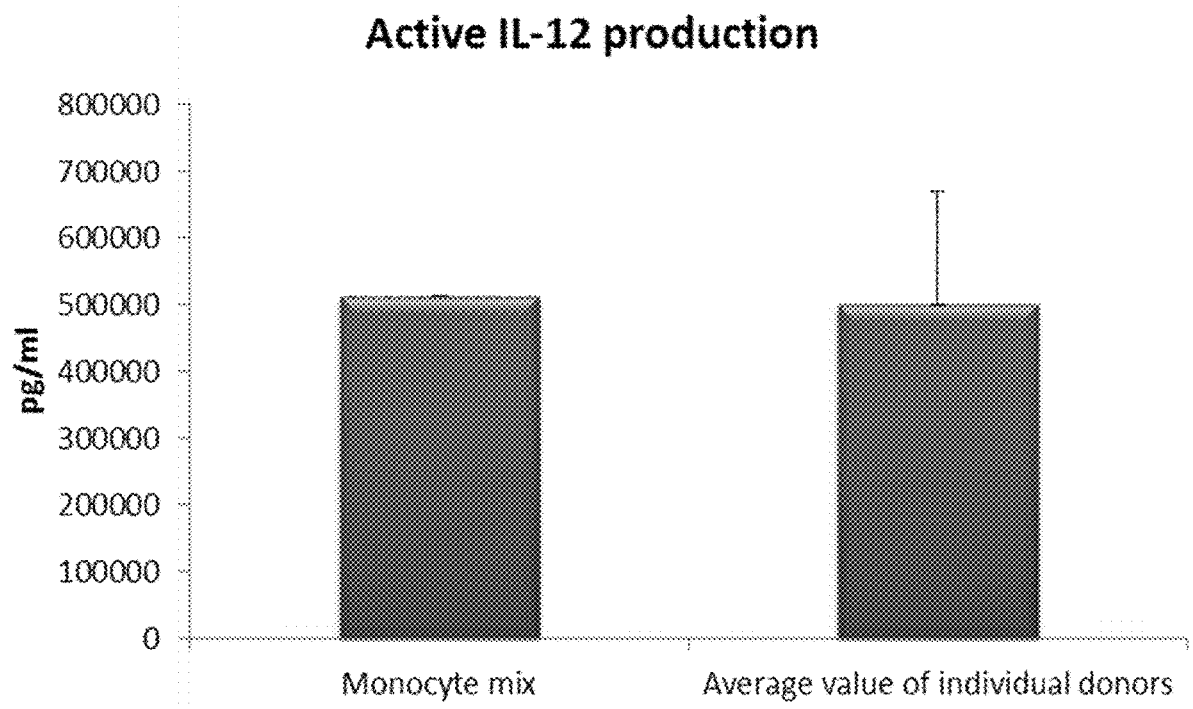
FIGS. 6A and 6B illustrate pro-inflammatory cytokine production by immature DCs (derived from single or mixed buffy coat monocyte cultures) during 18 hours of persistent stimulation with activating factors ("Active production").
Figure 6B:
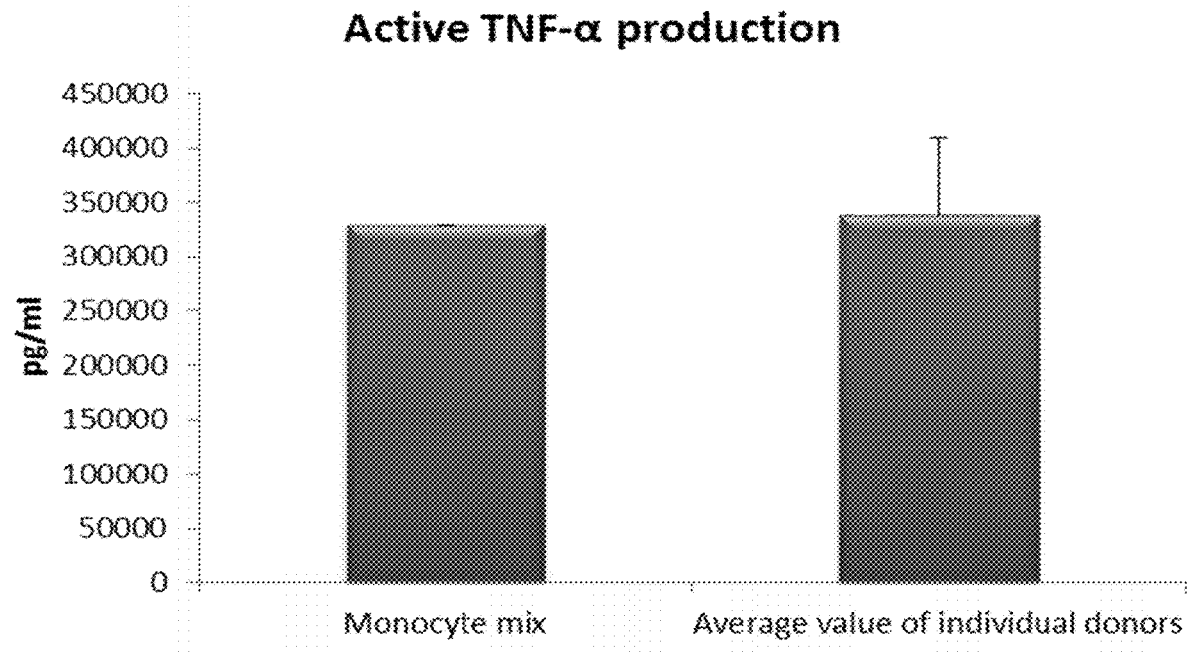
Figure 7A:
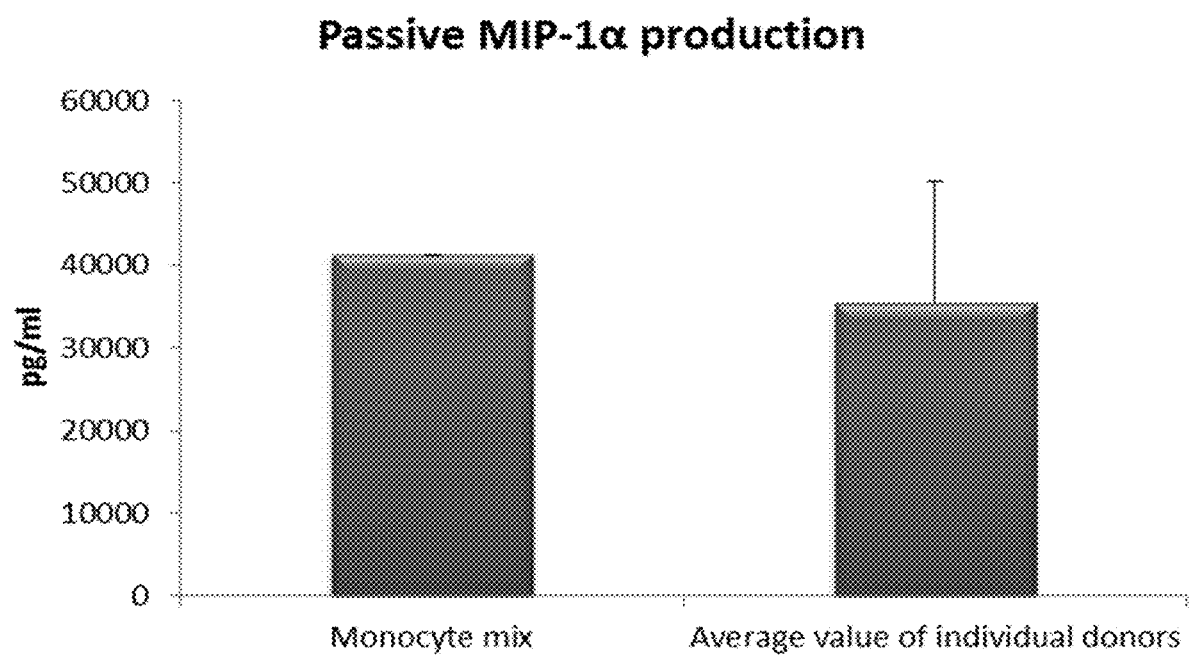
FIGS. 7A, 7B, 7C, and 7D illustrate pro-inflammatory chemokine production by PI-DCs (derived from single or mixed peripheral blood monocyte cultures). These PI-DCs have been washed after stimulation with activating factors for 18 hours and subsequently re-cultured for 24 hours without addition of activating factors ("Passive production").
Figure 7B:
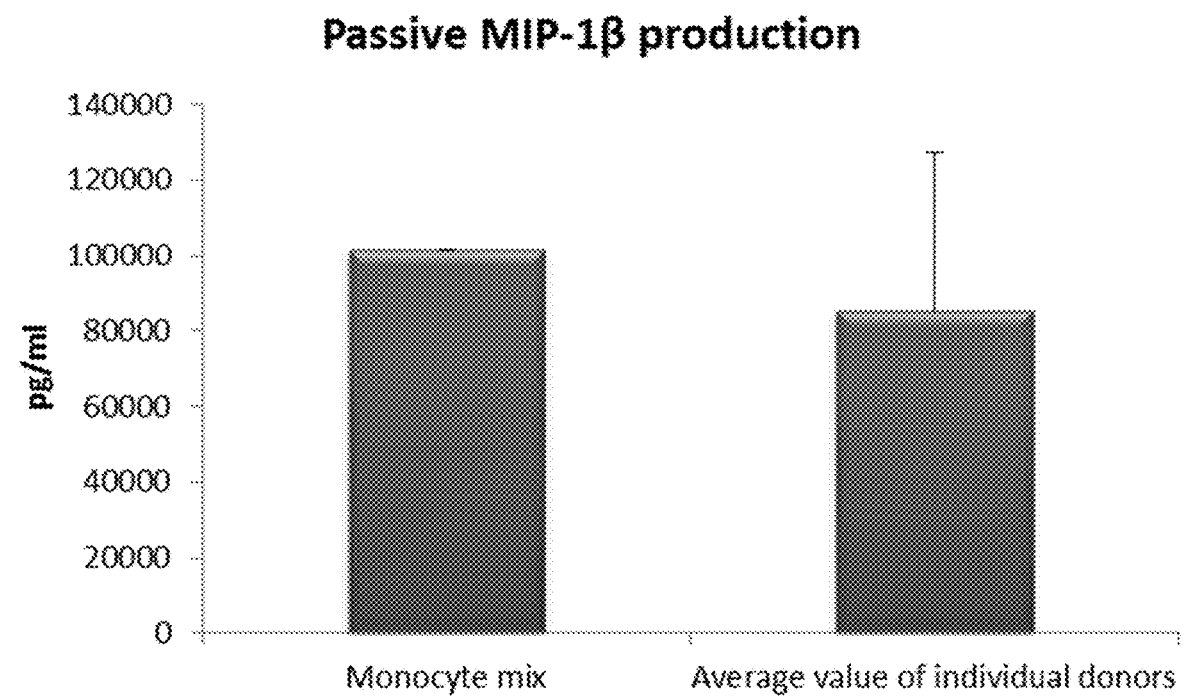
Figure 7C:
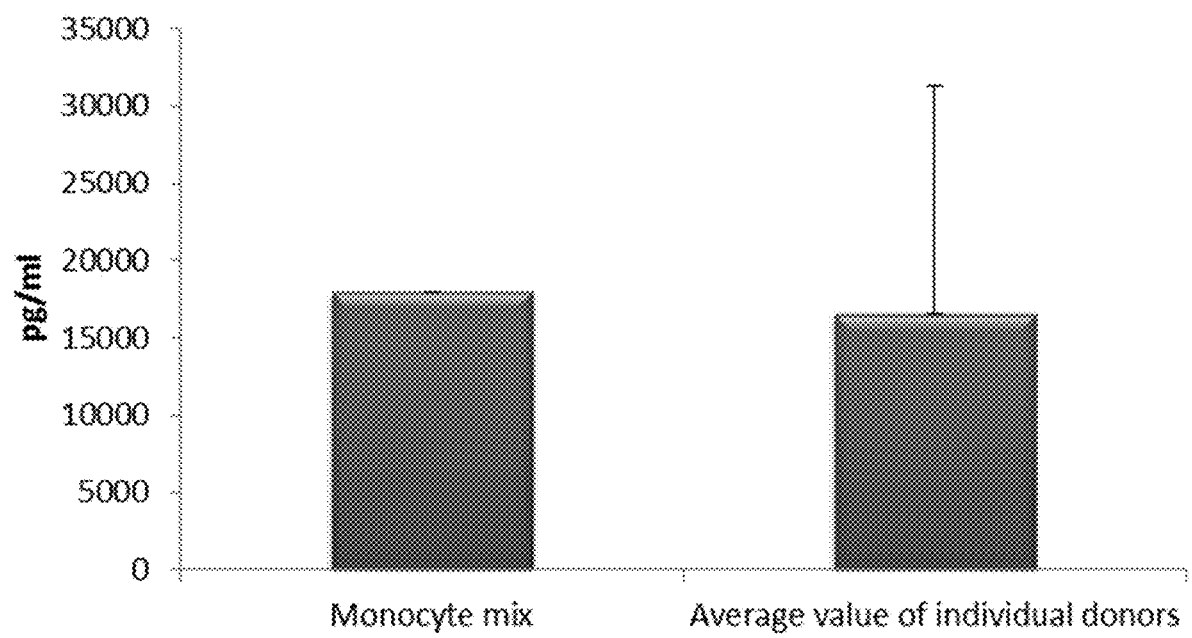
Figure 7D:
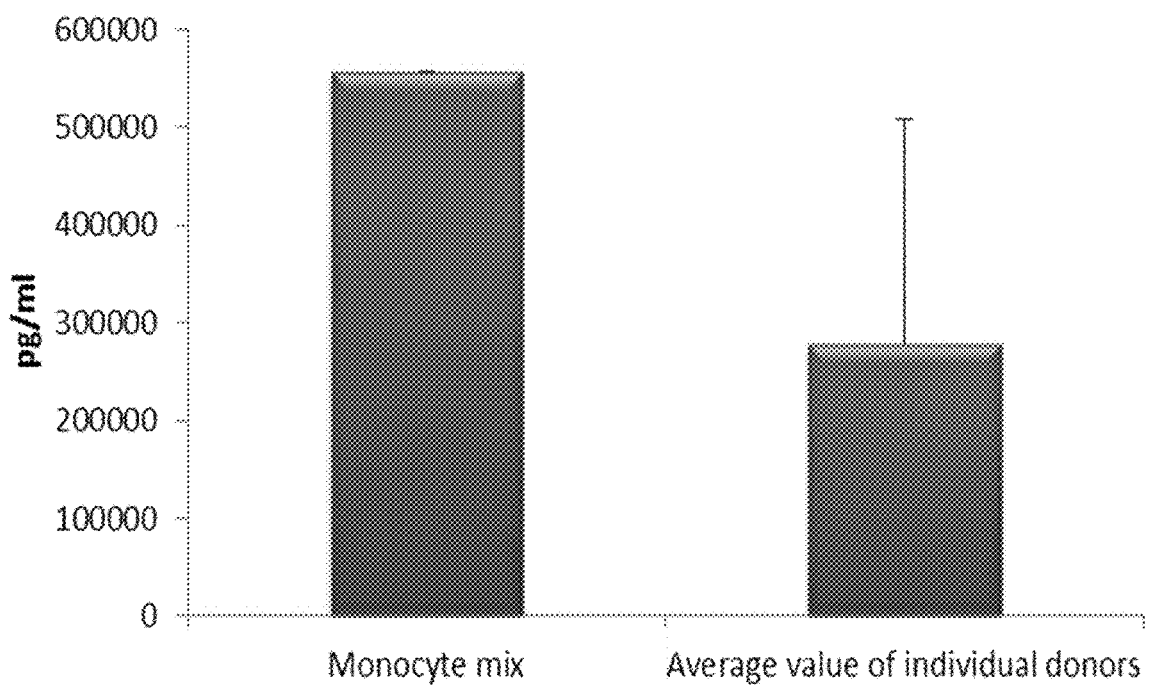

As seen in FIG. 6, the high, activation-induced, mean levels of IL-12p70 (FIG. 6A) and TNF-alpha (FIG. 6B) produced by "single" DCs was similar as compared to DCs derived from a monocyte-enriched leukocyte mixture of all three donors. Notably, there is a substantial variation in IL-12p70 and TNF-alpha production between different single-donor DCs.

Data were obtained from ELISA analysis. Results shown are mean values±SD from three individuals and the value obtained from the mixture of all three donors. The respective Y-axis shows the amount of the respective substance produced in pg/mL/$1\times10^6$ cells, during 18 hours of persistent stimulation/activation. The X-axis show the different combinations measured.

Figure 8A:
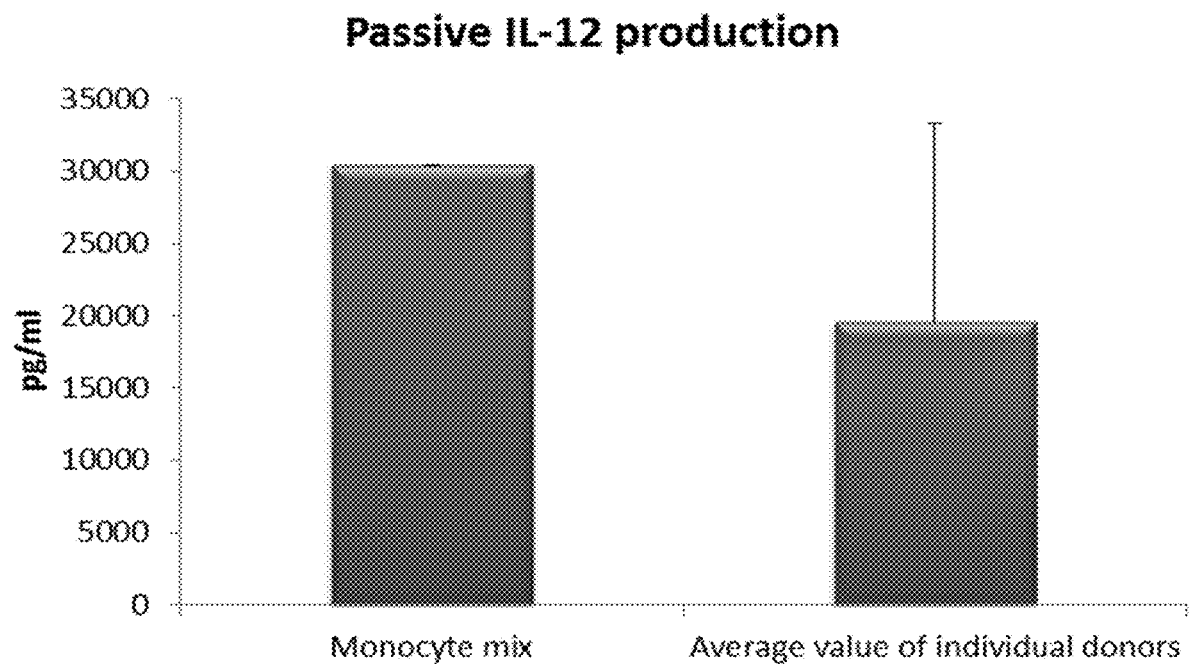
FIGS. 8A and 8B illustrate pro-inflammatory cytokine production by PI-DCs (derived from single or mixed peripheral blood monocyte cultures). These PI-DCs have been washed after stimulation with activating factors for 18 hours and subsequently re-cultured for 24 hours without addition of activating factors ("Passive production").
Figure 8B:
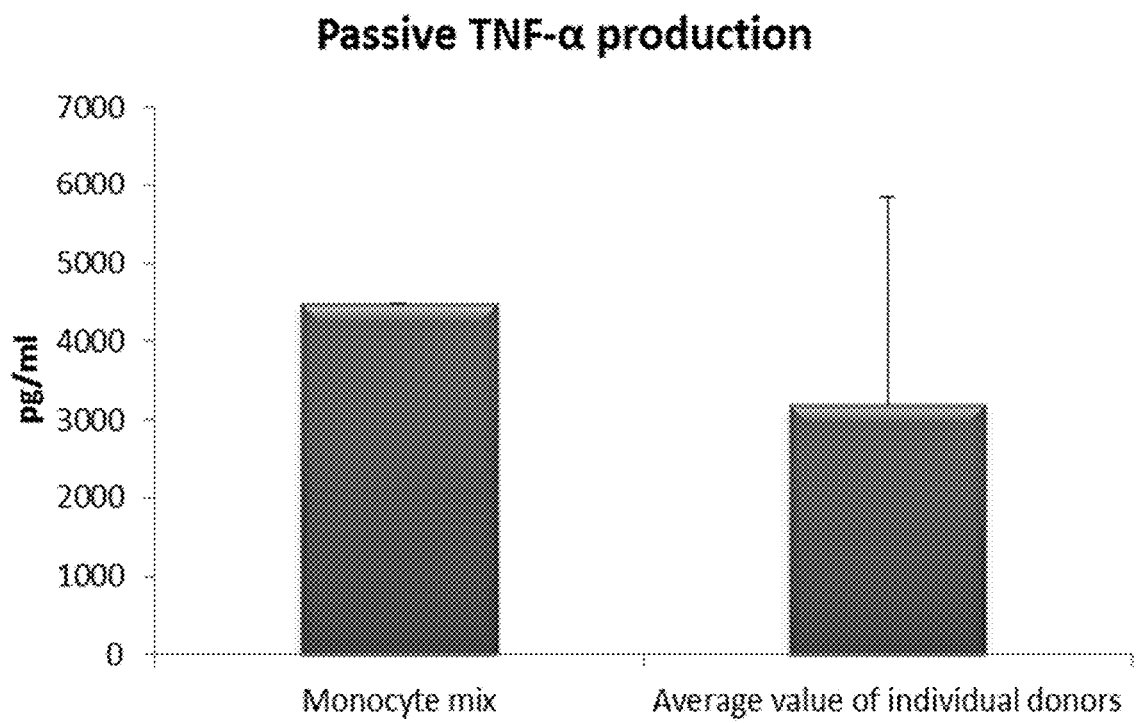
Figure 9A:
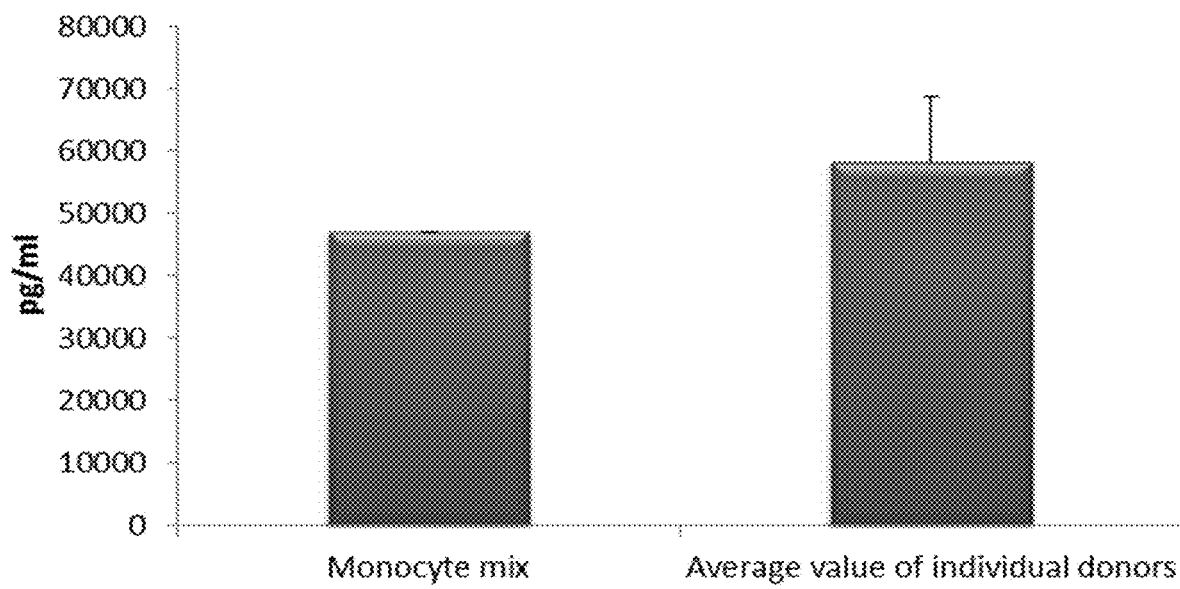
FIGS. 9A, 9B, 9C, and 9D illustrate pro-inflammatory chemokine production by PI-DCs (derived from single or mixed buffy coat monocyte cultures). These PI-DCs have been washed after stimulation with activating factors for 18 hours and subsequently re-cultured for 24 hours without addition of activating factors ("Passive production").
Figure 9B:
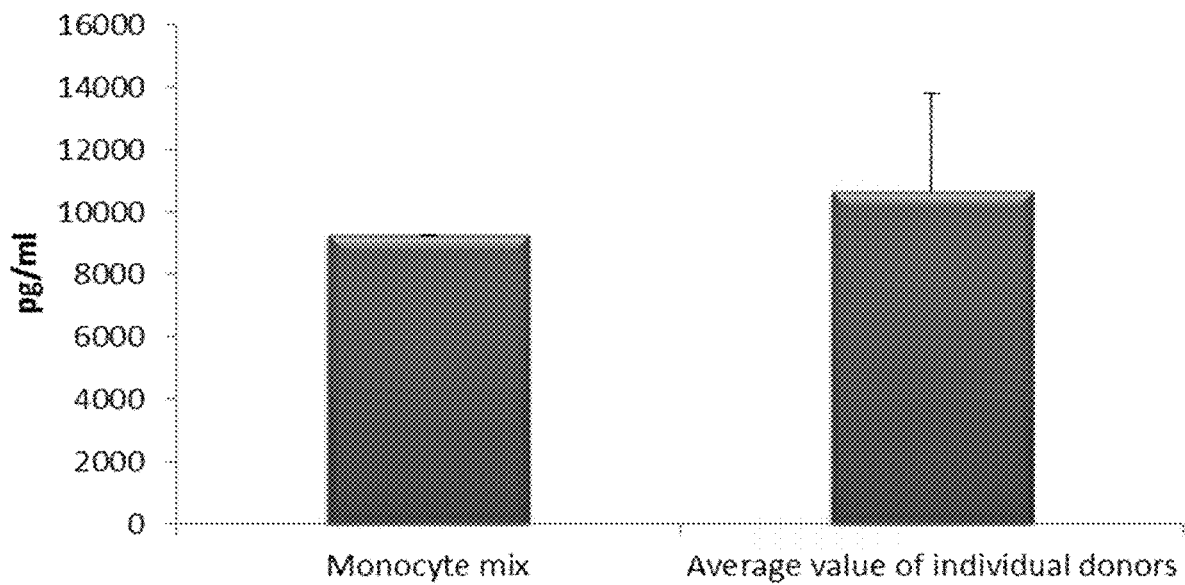
Figure 9C:
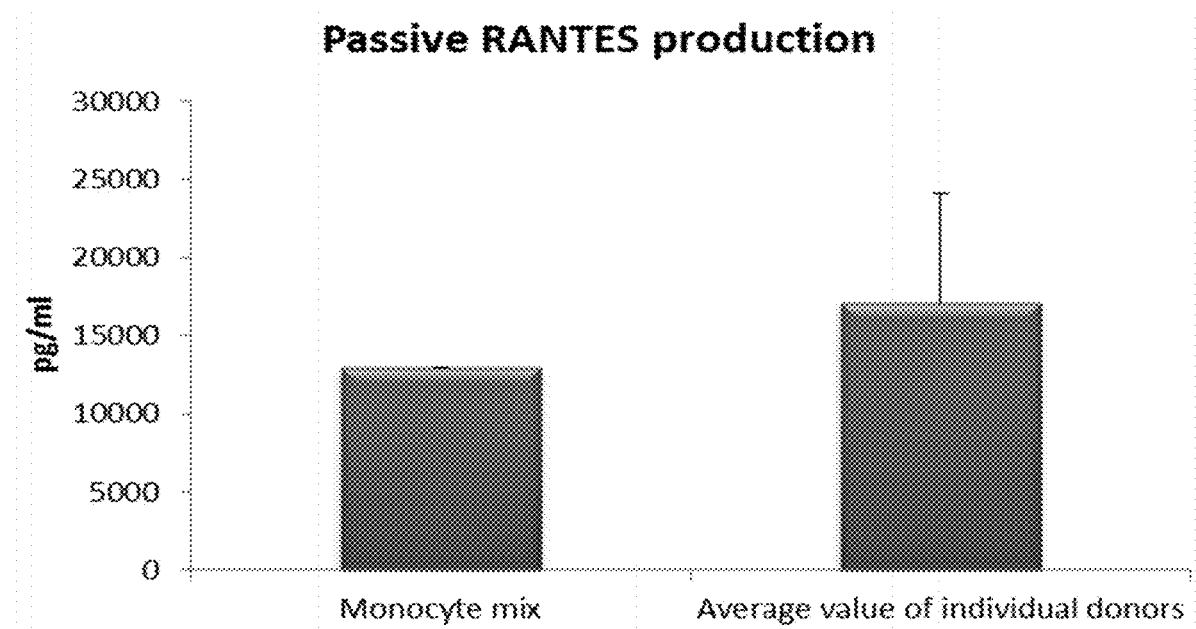
Figure 9D:
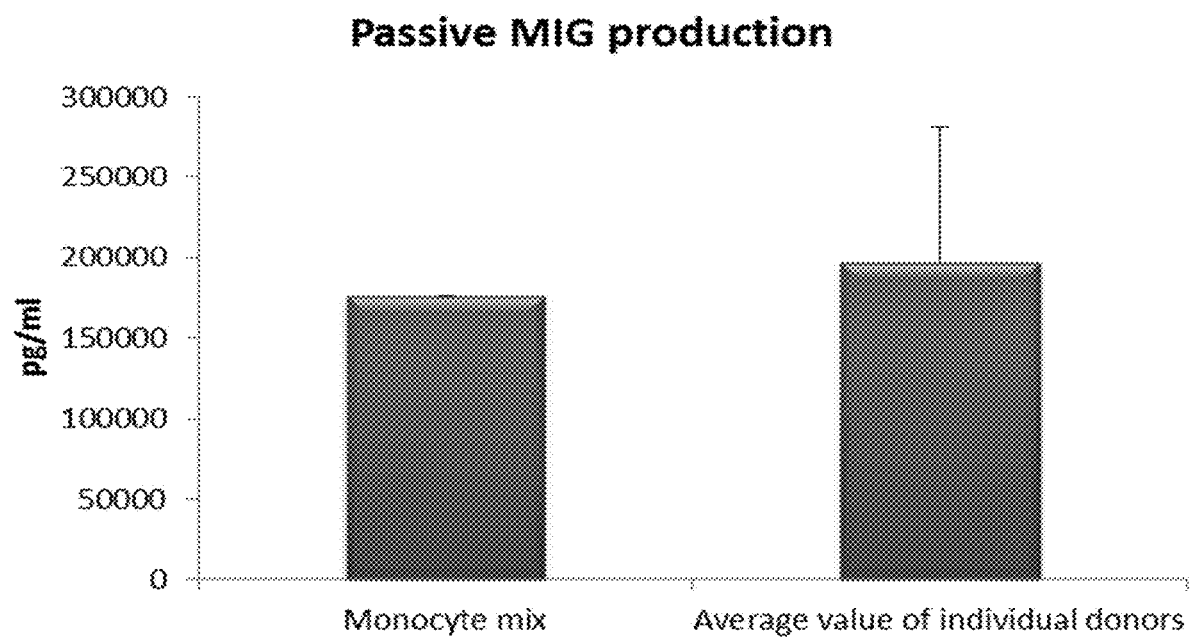

PI-DCs Derived from Co-Cultures of Mixed Allogeneic Peripheral Blood Monocytes Exhibit a Sustained Production of Pro-Inflammatory Chemokines and Cytokines In order to inject activated pro-inflammatory DCs (PI-DCs) into patients, they usually have to be washed prior to administration. If not, unwanted side-effect induced by the concurrent administration of stimulating agents (aimed to induce PI-DCs ex vivo) may occur. Immature DCs must therefore be activated into PI-DC with sustained production of desirable factors also after cessation of the activation-inducing factors. As seen in FIG. 7, the mean levels of MIP-1 alpha (FIG. 7A), MIP-1 beta (FIG. 7B), RANTES (FIG. 7C), MIG (FIG. 7D) produced by "single" PI-DCs after withdrawal of activating factors (PI-DCs from peripheral blood monocytes from three different donors analysed) was similar as compared to PI-DCs derived from a mixture of monocytes from all three peripheral blood donors. Notably, there is a substantial variation in chemokine production between different single donor PI-DCs after withdrawal of activation factors. The mean production of IL-12p70 (FIG. 8A) and TNF-alpha (FIG. 8B) produced by "single" PI-DCs after withdrawal of activating factors was also similar as compared to washed PI-DCs derived from a mixture of monocytes from of all three donors. Notably, there is a substantial variation in cytokine production between different single donor PI-DCs after withdrawal of activation factors.

Data were obtained from ELISA analysis. Results shown are mean values±SD from three individuals and the value obtained from the mixture of all three donors. The respective Y-axis shows the amount of the respective substance produced in pg/mL/$1\times10^6$ cells during 24 hours after withdrawal of activating factors. The X-axis show the different combinations measured.

Figure 10A:
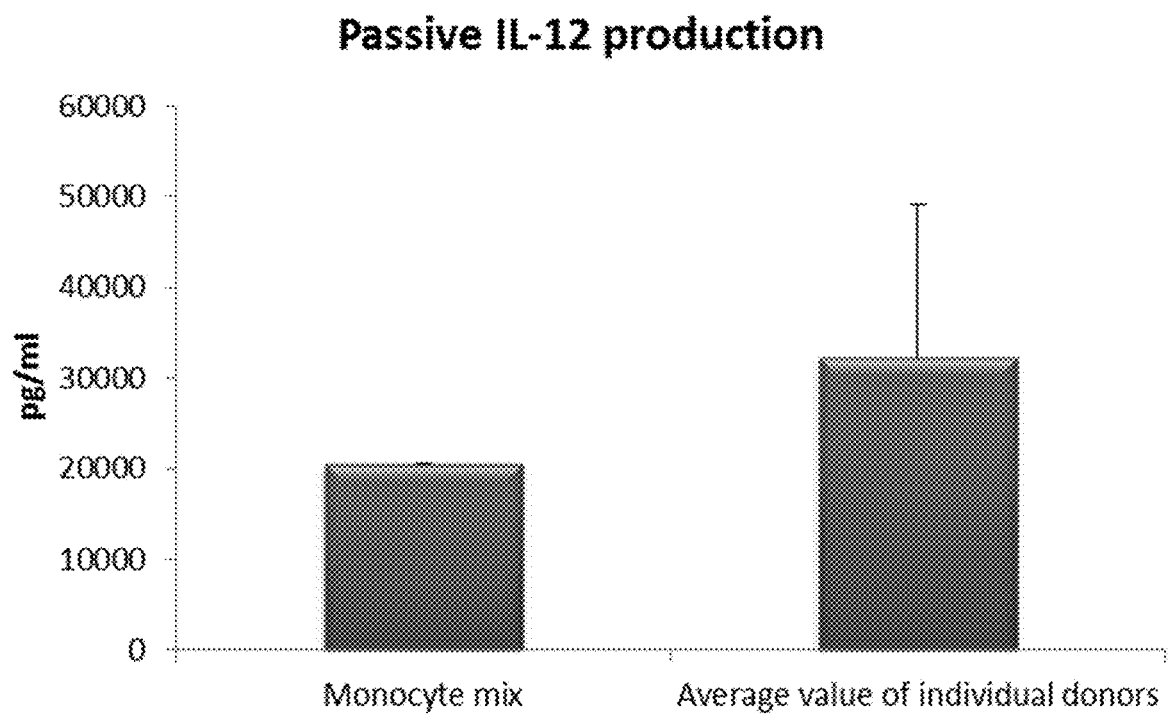
FIGS. 10A and 10B illustrate pro-inflammatory cytokine production by PI-DCs (derived from single or mixed buffy coat monocyte cultures). These PI-DCs have been washed after stimulation with activating factors for 18 hours and subsequently re-cultured for 24 hours without addition of activating factors ("Passive production").
Figure 10B:
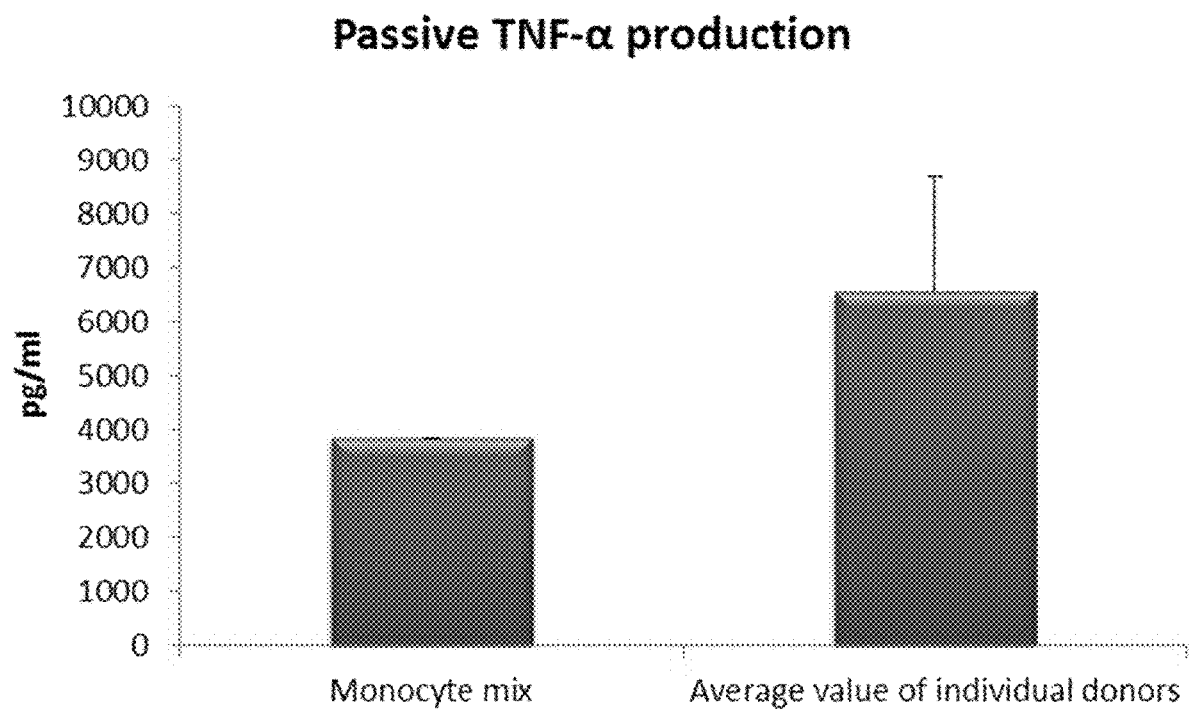

PI-DCs Derived from Co-Cultures of Mixed Allogeneic Monocyte-Enriched Peripheral Buffy Coat Leukocytes Exhibit a Sustained Strong Production of Pro-Inflammatory Chemokines and Cytokines As seen in FIG. 9, the mean level of MIP-1 alpha (FIG. 9A), MIP-1 beta (FIG. 9B), RANTES (FIG. 9C), MIG (FIG. 9D) produced by "single" PI-DCs after withdrawal of activating factors (PI-DCs from buffy coat monocytes from three different donors analyzed) was similar as compared to PI-DCs derived from a mixture of monocytes from all three buffy coat donors. Notably, there is a substantial variation in chemokine production between different single donor PI-DCs. The mean production of IL-12p70 (FIG. 10A) and TNF-alpha (FIG. 10B) produced by "single" PI-DCs after withdrawal of activating factors was also similar as compared to washed PI-DCs derived from a mixture of monocytes from of all three buffy coat donors. Notably, there is a substantial variation in cytokine production between different single donor PI-DCs.

Data were obtained from ELISA analysis. Results shown are mean values±SD from three individuals and the value obtained from the mixture of all three donors. The respective Y-axis shows the amount of the respective substance produced in pg/mL/1×10$^6$ cells during 24 hours after withdrawal of activating factors. The X-axis show the different combinations measured.

Figure 11A:
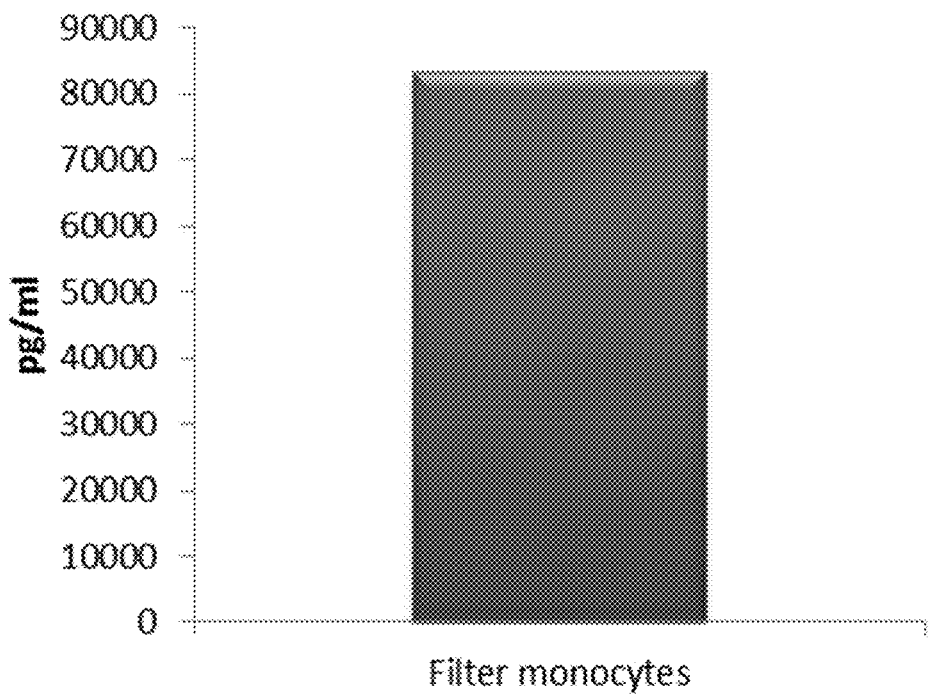
FIGS. 11A, 11B, 11C, and 11D illustrate that mixed immature DCs derived from filter monocytes produce substantial amounts of pro-inflammatory chemokines during 18 hours of persistent stimulation with activating factors ("Active production").
Figure 11B:
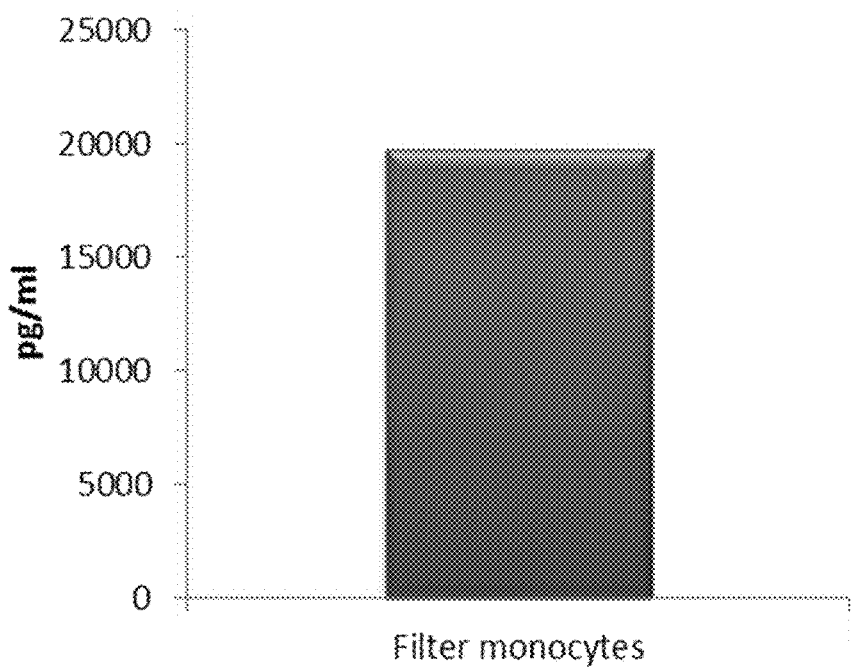
Figure 11C:
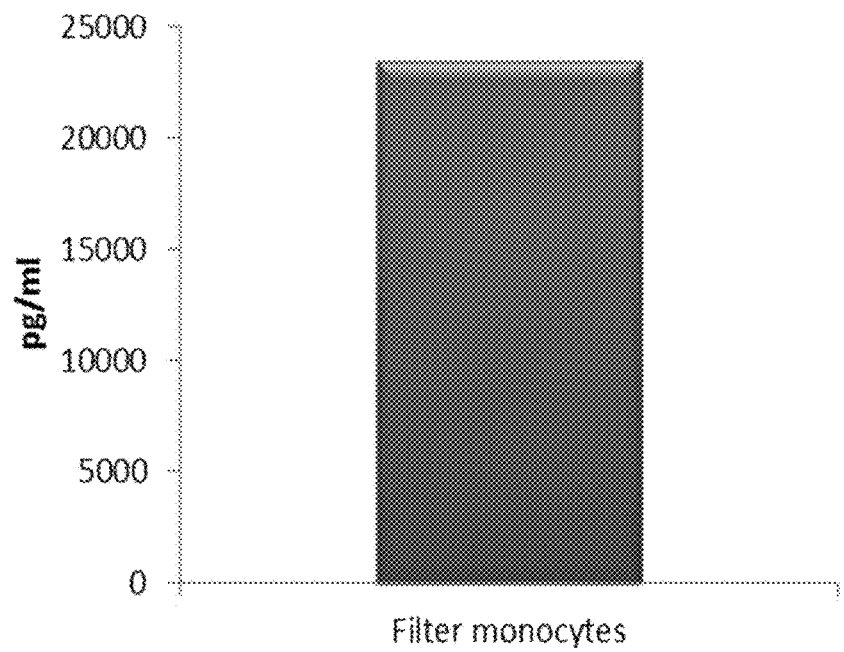
Figure 11D:
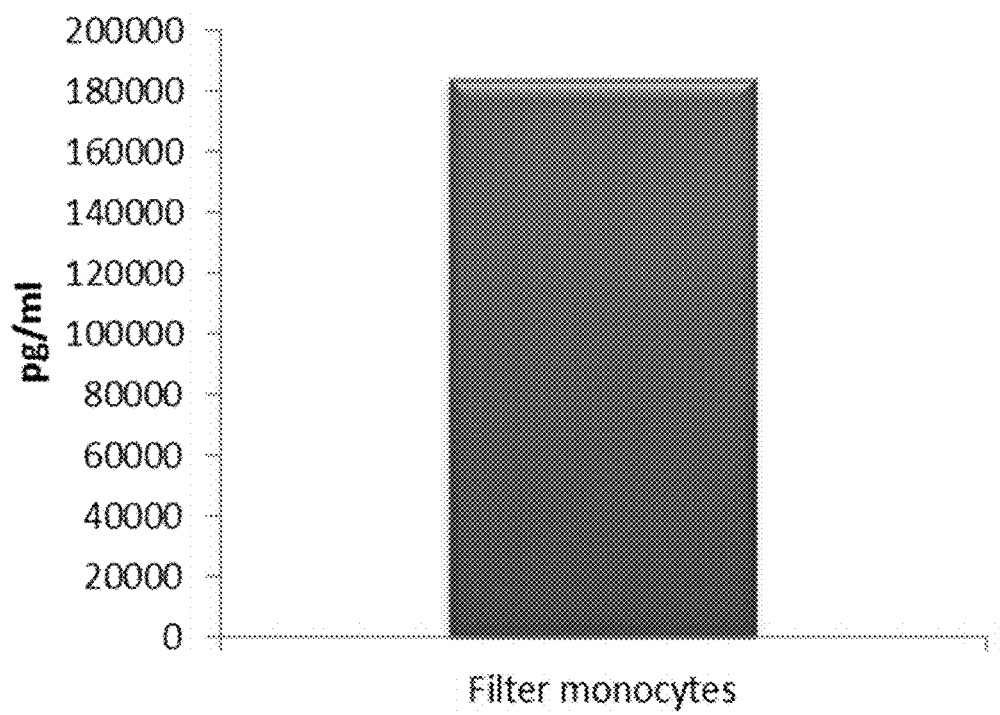
Figure 12A:
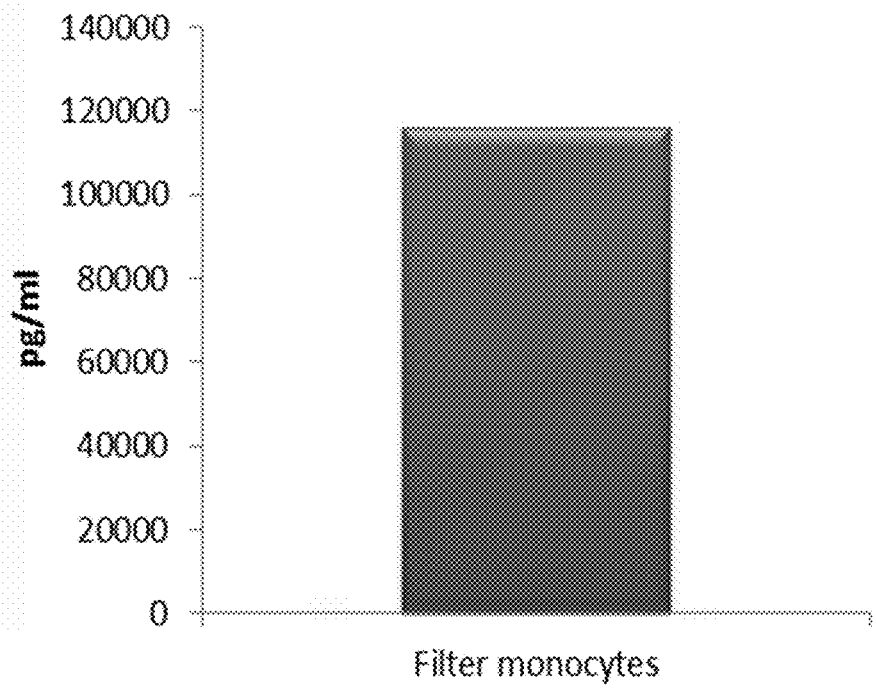
FIGS. 12A and 12B illustrate that mixed immature DCs derived from filter monocytes produce substantial amounts of pro-inflammatory cytokines during 18 hours of persistent stimulation with activating factors ("Active production").
Figure 12B:
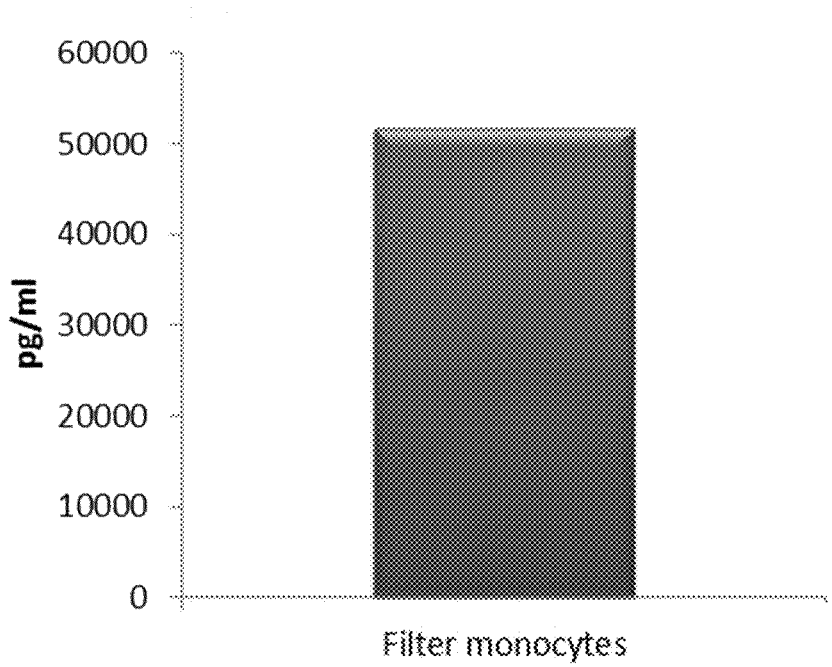
Figure 13A:
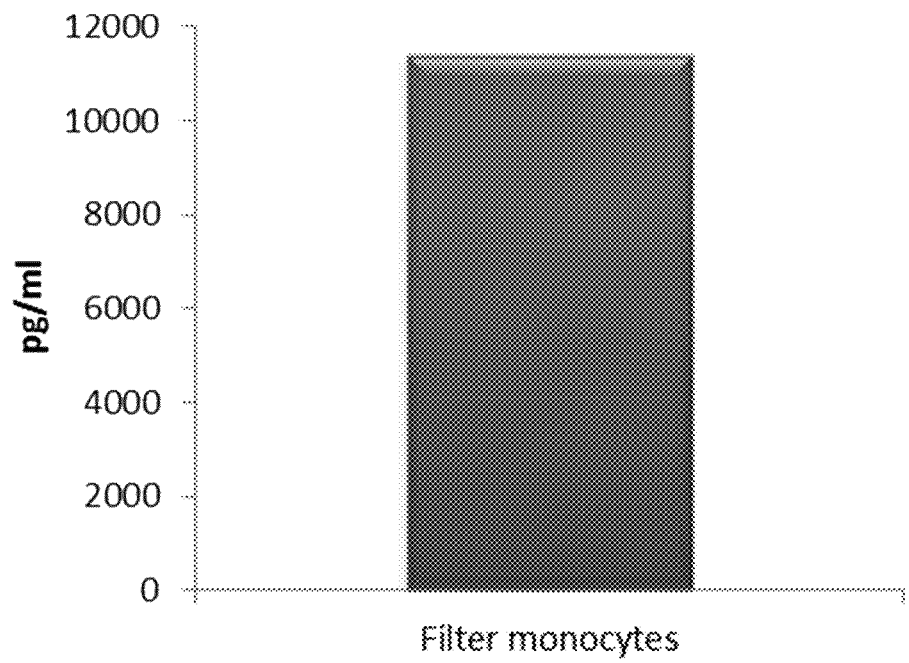
FIGS. 13A, 13B, 13C, and 13D illustrate that mixed PI-DCs derived from filter monocytes exhibit a substantial production of pro-inflammatory chemokines after withdrawal of activating factors. These PI-DCs have been washed after stimulation with activating factors for 18 hours and subsequently re-cultured for 24 hours without addition of activating factors ("Passive production").
Figure 13B:
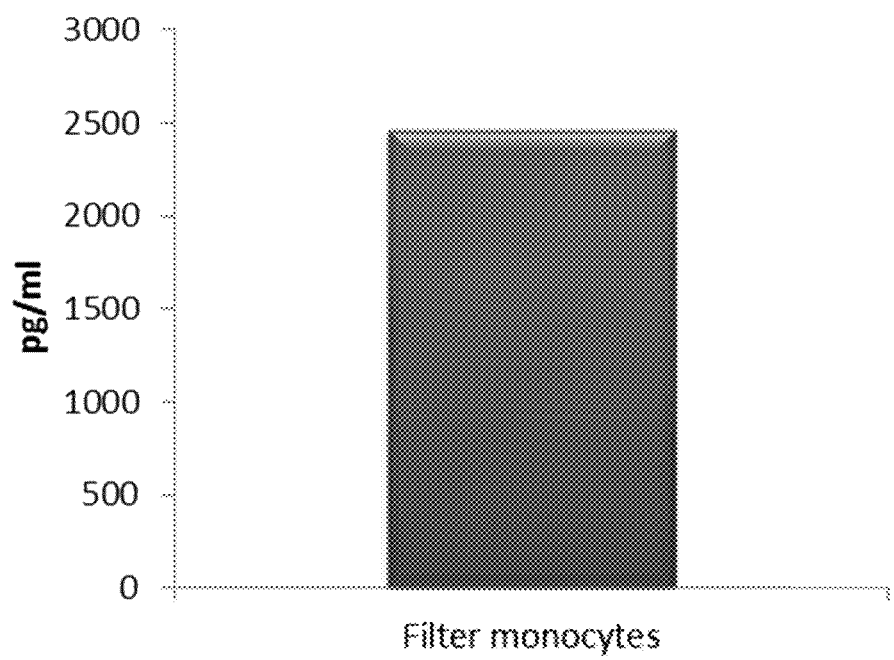
Figure 13C:
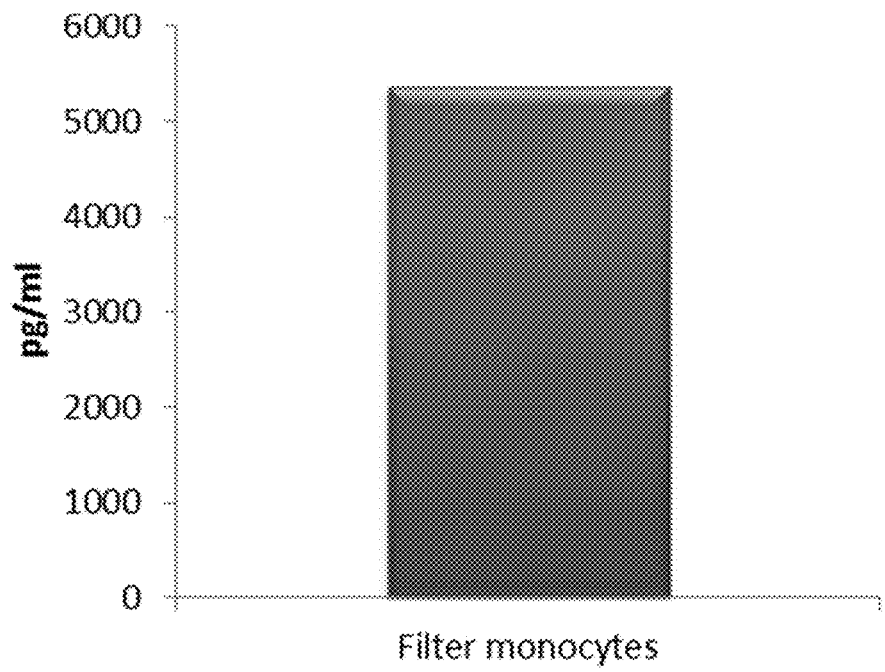
Figure 13D:
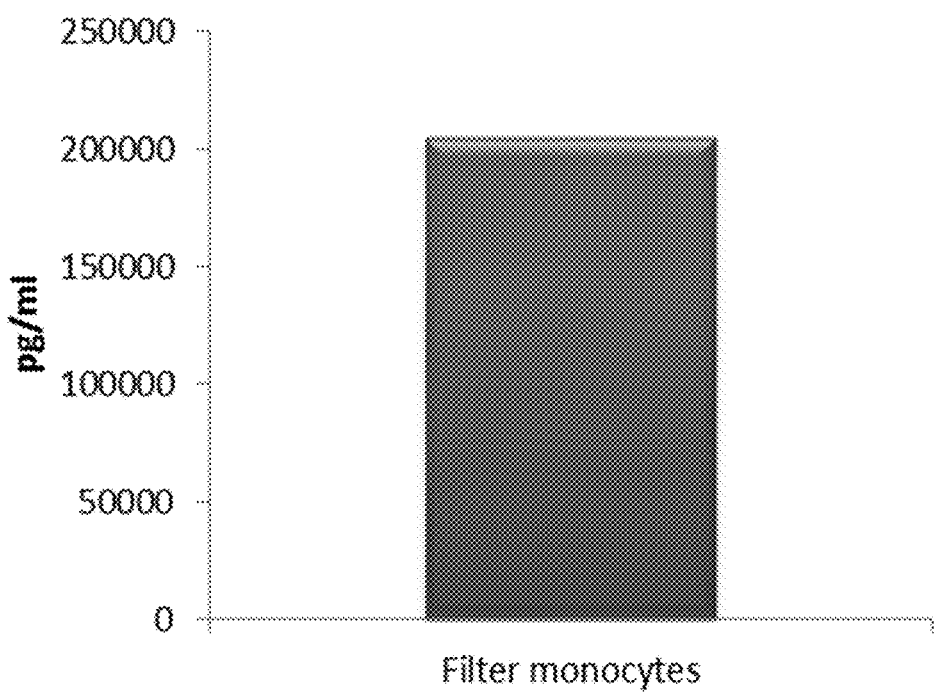

Mixed Immature DCs Derived from Monocyte-Enriched Filter Leukocytes Produce Substantial Amounts of Pro-Inflammatory Chemokines and Cytokines Upon Activation As seen in FIG. 11, activated mixed DCs derived from monocyte-enriched filter leukocytes (the initial leukocyte population was eluted from a 4-buffy coat leukocyte depletion filter) produced substantial amounts MIP-1 alpha (FIG. 11A), MIP-1 beta (FIG. 11B), RANTES (FIG. 11C), MIG (FIG. 11D). As seen in FIG. 12, a substantial amount of IL-12p70 (FIG. 12A) and TNF-alpha (FIG. 12B) was also produced.

Figure 14A:
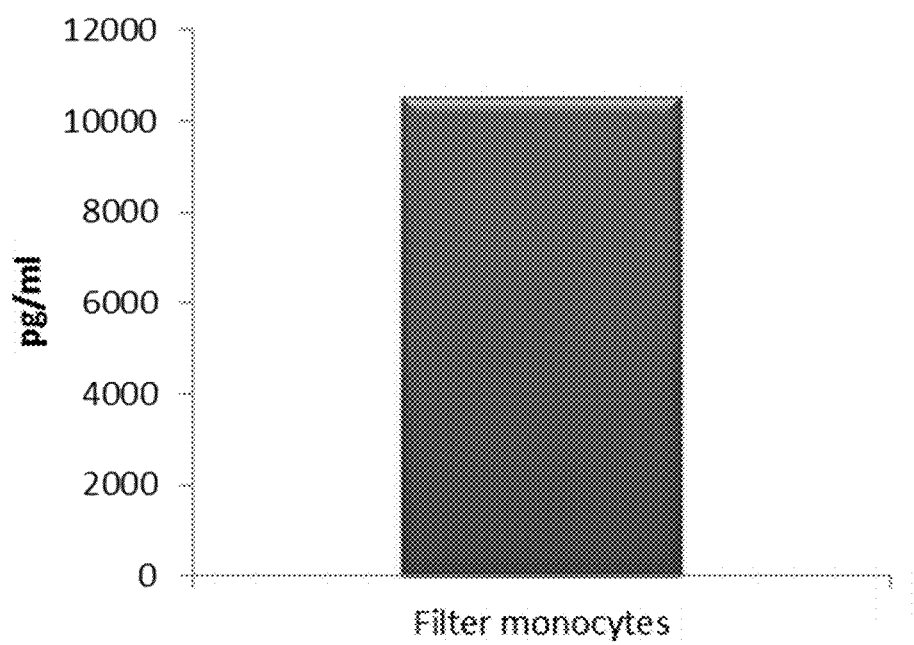
FIGS. 14A and 14B illustrate that mixed PI-DCs derived from filter monocytes exhibit a substantial production of pro-inflammatory cytokines after withdrawal of activating factors. These PI-DCs have been washed after stimulation with activating factors for 18 hours and subsequently re-cultured for 24 hours without addition of activating factors ("Passive production").
Figure 14B:
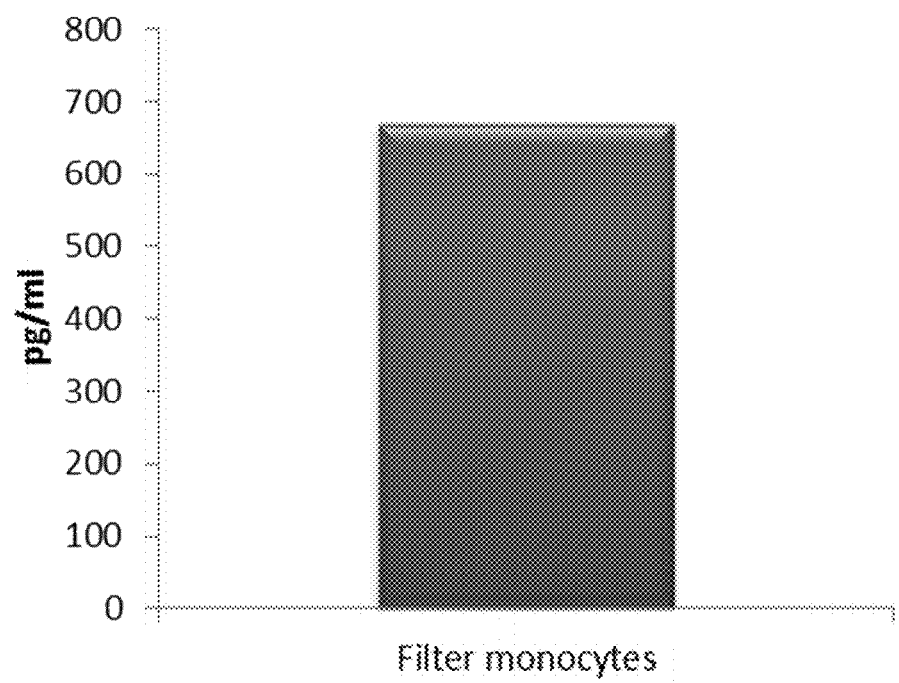

Data were obtained from ELISA analysis. Results shown are values from one experiment. The respective Y-axis shows the amount of the respective substance produced in pg/mL/1×10$^6$ cells, during 18 hours of persistent stimulation/activation Mixed PI-DCs Derived from Monocyte-Enriched Filter Leukocytes Exhibit a Substantial Production of Pro-Inflammatory Chemokines and Cytokines after Withdrawal of Activating Factors As seen in FIG. 13, activated mixed DCs derived from filter monocytes (the initial leukocyte population was eluted from a 4-buffy coat leukocyte depletion filter) produced substantial amounts MIP-1 alpha (FIG. 13A), MIP-1 beta (FIG. 13B), RANTES (FIG. 13C), MIG (FIG. 13D) after withdrawal of activating factors. As seen in FIG. 14, a substantial amount of IL-12p70 (FIG. 14A) and TNF-alpha (FIG. 14B) was also produced. Data were obtained from ELISA analysis. Results shown are values from one experiment. The respective Y-axis shows the amount of the respective substance produced in pg/mL/1×10$^6$ cells during 24 hours after withdrawal of activating factors.

The invention claimed is:

1. A method of producing pro-inflammatory dendritic cells (DCs), comprising the steps of:
providing a mixture of allogeneic leukocytes, which allogeneic leukocytes have been obtained from at least two different, allogeneic donors;
isolating allogeneic monocytes from said mixture of allogeneic leukocytes to provide monocyte-enriched allogeneic leukocytes;
generating non-exhausted immature DCs from said monocyte-enriched allogeneic leukocytes, wherein the generation of non-exhausted immature dendritic cells (DCs) is performed by co-culturing said monocyte-enriched allogeneic leukocytes for 2 to 7 days in aqueous cell culture medium free from non-human serum, said medium being supplemented with interleukin-4 (IL-4) and granulocyte-macrophage colony stimulating factor (GM-CSF); and
activating the non-exhausted immature DCs to obtain pro-inflammatory DCs, wherein said activation is performed by addition of Toll-like receptor 3 (TLR3)-ligand poly-I:C, a TLR7/8-ligand selected from the group consisting of Resiquimod, Gardiquimod and Imiquimod, and interferon gamma (IFN-γ) to induce activation.

2. The method according to claim 1, wherein said cell culture medium comprises at least one human polypeptide.

3. The method according to claim 2, wherein said human polypeptide is selected from the group consisting of transferrin, albumin, and insulin.

4. The method according to claim 1, wherein said monocyte-enriched allogeneic leukocytes comprise allogeneic neutrophils.

5. The method according to claim 1, wherein said mixture of allogeneic leukocytes is provided by pooling of at least two buffy coats comprising leukocytes, said buffy coats to be pooled being obtained from at least two different, allogeneic donors.

6. The method according to claim 5, wherein said pooled buffy coats contain platelets or are platelet depleted.

7. The method according to claim 1, wherein said mixture of allogeneic leukocytes is provided by:
eluting leukocytes from at least two leukocyte depletion filters, which filters, respectively, previously have been used to deplete leukocytes from whole blood, said whole blood being obtained from at least two different allogeneic donors; and
pooling the obtained leukocytes to obtain said mixture of allogeneic leukocytes; or by
eluting leukocytes from a leukocyte depletion filter, which filter has been used to deplete leukocytes from pooled buffy coats, wherein the pooled buffy coats originate from at least two different, allogeneic donors.

8. The method according to claim 1, wherein said allogeneic monocytes are isolated by elutriation or by antibody/bead isolation.

9. The method according to claim 1, wherein said co-culturing is performed for about 5 days.

10. The method according to claim 1, further comprising the step of loading the non-exhausted immature DCs with an antigen.

11. The method according to claim 1, wherein the immature DCs are exposed to the activation factors for 8 to 24 hours, whereafter essentially all of the activation factors are washed away.

* * * * *